United States Patent [19]
Hildebrandt et al.

[11] Patent Number: 6,009,748
[45] Date of Patent: Jan. 4, 2000

[54] RAPIDLY CYCLABLE FOAM TESTING OVEN

[75] Inventors: Marc J. Hildebrandt, Midland; Joseph S. Trombley, Auburn; James R. Cotter, Bay City; Theodore W. Selby, Midland, all of Mich.

[73] Assignee: Tannas Co., Midland, Mich.

[21] Appl. No.: 09/122,350

[22] Filed: Jul. 24, 1998

Related U.S. Application Data

[63] Continuation-in-part of application No. 08/782,822, Jan. 13, 1997, Pat. No. 5,824,886
[60] Provisional application No. 60/057,686, Aug. 27, 1997.

[51] Int. Cl.⁷ .............................. G01N 37/00; H05B 3/06
[52] U.S. Cl. .......................... 73/60.11; 219/523; 219/531
[58] Field of Search ............................... 73/60.11, 61.46, 73/866, 53.01, 53.05; 219/521, 522, 523, 535

[56] References Cited

U.S. PATENT DOCUMENTS

| | | |
|---|---|---|
| 785,524 | 3/1905 | Shea . |
| 1,673,333 | 6/1928 | Klumpp . |
| 1,694,725 | 12/1928 | Tabb . |
| 1,763,461 | 6/1930 | Fowler . |
| 1,829,600 | 10/1931 | McGregor . |
| 2,299,401 | 10/1942 | Melton . |
| 2,380,679 | 7/1945 | Smith . |
| 2,418,254 | 4/1947 | Fleharty . |
| 2,907,861 | 10/1959 | Melton . |
| 3,027,755 | 4/1962 | Groll et al. . |
| 3,028,473 | 4/1962 | Dyer et al. . |
| 3,779,731 | 12/1973 | Pollock et al. . |
| 3,971,630 | 7/1976 | Sanbrock et al. . |
| 4,073,697 | 2/1978 | Uchiyama . |
| 4,356,967 | 11/1982 | Lunick . |
| 4,572,427 | 2/1986 | Selfridge et al. . |
| 4,577,491 | 3/1986 | Callaghan et al. . |
| 4,678,752 | 7/1987 | Thorne et al. . |
| 5,154,088 | 10/1992 | Lehnert et al. . |

(List continued on next page.)

FOREIGN PATENT DOCUMENTS

| | | |
|---|---|---|
| 0252738 | 1/1988 | European Pat. Off. . |
| 1186105 | 4/1970 | United Kingdom . |
| 1313970 | 4/1973 | United Kingdom . |
| 2157833 | 10/1985 | United Kingdom . |
| 2169086 | 7/1986 | United Kingdom . |
| 2310612 | 9/1997 | United Kingdom . |

OTHER PUBLICATIONS

Catalog, Arthur H. Thomas Co, 1974, pp. 102; 1034; 1223; 1347 & 1348.

(List continued on next page.)

*Primary Examiner*—Hezron Williams
*Assistant Examiner*—Jay L. Politzer
*Attorney, Agent, or Firm*—Christopher John Rudy

[57] ABSTRACT

Oven, for example, embodied as a foam tester, can heat and cool circulating gas, and hence, contained sample containers, rapidly. A volume for containing coolant material is provided for cooling the oven volume is provided apart from the oven volume, and the cooling volume is adapted to contain cooling material, at least during operation of the cooling cycle. Optionally, the cooling volume can be closed off from the oven volume when the device is in heating mode and opened when in cooling mode, but preferably, it is not but has a drainable liquid, for example, water, cooling system installed in the cooling volume. The device may have an air plume; preferably however, it has such a plume eliminated with high circulation blowing and mixing of the bath gas, for example, air, provided. Accessories such as a removable drain tray, and so forth, may be added. The exemplary devices are particularly useful for testing for the foaming characteristics of liquids, and the principles of the cooling volume can be applied to cabinet ovens in general. As an option, gel or cooling other than liquid in radiator cooling, for example, solid state cooling, may be employed. Test methodology can include injection of a gas to include a preheated gas, for example, air, into an oleaginous liquid sample, for example, oil or transmission fluid, especially having standardized, predetermined level(s) of contaminant (s).

13 Claims, 14 Drawing Sheets

U.S. PATENT DOCUMENTS

| | | |
|---|---|---|
| 5,271,085 | 12/1993 | Carballo . |
| 5,336,866 | 8/1994 | Winstead et al. . |
| 5,456,147 | 10/1995 | Stange, Jr. . |
| 5,460,441 | 10/1995 | Hastings et al. . |
| 5,465,610 | 11/1995 | Loisel . |
| 5,466,364 | 11/1995 | Kaul et al. ............... 208/307 |
| 5,501,839 | 3/1996 | Tarantino . |
| 5,549,473 | 8/1996 | Valentian . |
| 5,597,950 | 1/1997 | Mullen . |
| 5,661,978 | 9/1997 | Holmes et al. . |
| 5,824,886 | 10/1998 | Selby et al. ............... 73/60.11 |
| 5,891,732 | 4/1999 | Prins et al. ............... 436/24 |

OTHER PUBLICATIONS

ASTM D 892–92, ASTM, May, 1992.

Lubrication Technology, Savant, Inc. Sep., 1996.

Technical Bulletin No. 4, Tannos Co., Dec., 1996.

RAPIDLY CYCLABLE FOAM TESTING OVEN

CROSS-REFERENCES

This is a continuation-in-part of application Ser. No. 08/782,822 filed on Jan. 13, 1997, now U.S. Pat. No. 5,824,886 issued on Oct. 20, 1998. This also claims the benefit under 35 USC 119(e) of provisional application 60/057,686 filed on Aug. 27, 1997.

BACKGROUND TO THE INVENTION

I. Field of the Invention

This invention concerns a circulating gas oven, cyclable from heating to cooling modes. It is particularly useful for testing the foaming of liquids at elevated temperatures.

II. Description of Arts, Problems, and Needs, Including Information Disclosed Per 37 CFR 1.56, 1.97 & 1.99

As set forth in Selby et al., U.S. patent application Ser. No. 08/782,822 filed on Jan. 13, 1997, now U.S. Pat. No. 5,824,886, one of the problems with liquids, including lubricants, is foam which can form under operating conditions. In order to test this, and in the process determine a standard property of such liquids, techniques such as the ASTM-D-892 test method have been used for some time. In the ASTM-D-892 test method, foaming characteristics of lubricating oils are determined at temperatures up to ninety-three and one half degrees Celsius. An air bubbling stone is set in the sample; the sample is heated appropriately as air is bubbled in, and foam characteristics of the sample are observed over a period of time. However, with the advent of modern engines, the oils and other lubricants which are employed in the engines are made subject to higher and higher operating temperatures. Thus, it becomes desirable to test for the characteristics of such fluids at or above such temperatures, and among such desired tests is a high temperature foaming test, up to and above one hundred fifty degrees Celsius. However that may be, currently available liquid-filled baths to test for and monitor foam characteristics, and in particular as might be encountered at high temperatures, have several drawbacks. Among these are included the following:

1) A lack of an ability to heat and cool quickly.
2) A lack of ability to see through the bath liquid.
3) Requirement of more than one bath.
4) Requirement of frequent bath liquid changes.
5) Difficulty of handling sample containers coming from the liquid bath and coated with hot oil—plus hot cabinetry.
6) Difficulty of operation.

In addressing such matters, the aforementioned Selby et al. application, which incorporated and claimed the benefit of U.S. provisional patent application Serial Nos. 60/012,576 filed on Feb. 29, 1996 and 60/026,429 filed on Sep. 20, 1996, in brief, disclosed a gas, and especially air, bath foam tester having an insulated cabinet with a temperature-regulatable volume contained therein; a heater capable of heating a gas for the volume; a feature to circulate heated gas in the volume; an access system such that sample container(s), each capable of holding a liquid sample, is(are) insertable into the volume so that the same can be heated therein; and a feature to observe any sample(s) in the sample container(s) such that observation can be conducted from outside the cabinet—and further wherein cooling can be provided by water or other liquid and/or by insert of a cooling device, for example, an insert in place of a foam tester sample "carousel" or an insert which may penetrate the side of the cabinet. A foam testing protocol was disclosed in which the heating mode of the device was alternated with a cooling mode so that samples could be tested more quickly in the same device. As well, a special pourable sample container was provided thereby.

As significant as that invention is to the art—and it has commercial ramifications as showed by Savant, Inc., Lubrication Technology, "Foam Testing Now Available," September 1996, it is not without drawbacks. Chief among these is that, according to an ever-present drive to improve efficiencies, that foam tester can take longer to cool down between tests than desired.

The following art was cited by the U.S. examiner in the first action in the aforesaid '822 application:

Smith et al., U.S. Pat. No. 2,380,679. This discloses an apparatus for testing the foaming characteristics of liquids, more particularly, an oil-submersible aerator.

Groll, Jr., et al., U.S. Pat. No. 3,027,755. This discloses an apparatus and method for determining effectiveness of defoamers in foamy systems, more particularly, in strippable foamy system, i.e., a fluid system which upon agitation results in the production of froth or foam and containing one or more components which are to be stripped or removed therefrom, e.g., a synthetic rubber lattice produced by copolymerizing unsaturated compounds such as 1,3-butadiene and styrene.

Callaghan et al., U.S. Pat. No. 4,577,491. This discloses a method for determining the stability of foam, which includes a sample pressurizing vessel connected to a sample injection chamber leading to a sample cell linked to a reference cell maintained at constant pressure.

Lehnert et al., U.S. Pat. No. 5,154,088. This discloses apparatuses and methods for incorporating blowing agents into liquids for the production of polymer foams and for measuring the volumetric expansion potential of mixtures thereof. An apparatus thereof includes a high pressure liquid storage and mixing tank.

Winstead et al., U.S. Pat. No. 5,336,866. This discloses a fabric sample treatment apparatus, which is for effecting the controlled and uniform heating of a plurality of fabric and dye liquor specimens, and which includes a heating chamber having a rotatable sample rack, a radiant heat source, multidirectional cooling air vents, temperature measurement devices for monitoring chamber and specimen temperature, and control equipment.

Loisel, U.S. Pat. No. 5,465,610. This discloses a device for the characterization of the foaming properties of a product which is at least partially soluble, which includes a transparent analysis column with a porous base to introduce a gas flow, and an automatic measuring system.

Mullen, U.S. Pat. No. 5,597,950. This discloses surfactant monitoring by foam generation, a device of which detects the formation of foam with a light beam or conductivity measurement.

Arthur H. Thomas Co., Philadelphia, Pa., 1974 Parts Catalog, page 102. This discloses glass beakers.

The following art was initially cited by the U.K. examiner in a search report dated May 22, 1997 in British patent application No. GB 9704236.0 corresponding to the aforesaid '822 application:

Lunick, U.S. Pat. No. 4,356,967. This discloses a laboratory incubator chamber system, which includes an air-tight sealed compartment for providing an incubation chamber and a sealed control compartment for housing electronic circuitry.

Selfridge et al., U.S. Pat. No. 4,572,427. This discloses a controlled atmosphere enclosure, which is an incubator having a housing defining a thermally insulated chamber with a controlled gas atmosphere. Sensing devices are in a gas recirculation path outside the incubator chamber. The gas atmosphere circulates from a chamber outlet in an upper portion of the chamber, through the recirculation path, returning to the incubator chamber through an inlet in a lower portion of the chamber. Included in the recirculation path are a recirculation blower, a filter, a carbon dioxide sensor, and a humidifier.

European patent application publication No. 0 252 738 A2. This discloses a foam meter, which includes a thermostatically controlled column open at one end with a mesh at the other end.

U.K. patent specification No. 1,186,105. This discloses a humidity cabinet, which includes a plurality of moisture-proof compartments for samples to be tested, each compartment having a door which can be opened or closed as desired, a fan in each compartment, a common drive means for the fans located outside the compartments, and a timing device controlling the operation of the fans.

U.K. patent specification No. 1 313 970. This discloses an apparatus for laboratory testing of sustained release drugs, which includes a heatable chamber, means for accurately controlling the temperature in the chamber and including a mercury bulb thermometer located within the chamber, a relay operating switch connected to a heat source for the chamber, and a rotatable wheel-shaped device located within the chamber and supporting a number of elution bottle housings.

U.K. patent application No. GB 2 157 833 A. This discloses testing oil for emulsion formation, which includes a test rig—meant to simulate engine operating conditions so as to determine the propensity of various oils to form water-in-oil emulsions in the rocker covers of the engine—in which heated oil and heated saturated air, or raw steam, are directed by delivery pipes onto an inclined test plate disposed inside a cabinet and cooled.

U.K. patent application No. GB 2 169 086 A. This discloses an apparatus for testing of fluids, especially for physical characteristics or susceptibility of process fluids, e.g., oil, to foam or form an emulsion, which includes a rotor with at least one arcuate and preferably transparent pipe segment that can transport the test fluid at various speeds during the rotation.

SUMMARY

The present invention provides in a foam tester including an insulated cabinet with a temperature-regulatable oven volume contained therein; a heater capable of heating a gas for the oven volume; a feature to circulate heated gas in the oven volume; an access system such that sample container (s), each capable of holding a liquid sample, is(are) insertable into the oven volume so that the same can be heated therein; and a feature to observe any sample(s) in the sample container(s) such that observation can be conducted from outside the cabinet—and wherein a cooling feature is provided to cool down the oven volume in the insulated cabinet—the improvement which comprises a cooling volume apart from the oven volume for containing coolant material, optionally, which can be closed off from the oven volume when the device is in heating mode and vice versa, preferably, however, which is not, but has a drainable liquid cooling system installed therein. In one particular embodiment, gel cooling may be employed; in another, high volume blowers circulate oven air, which can be cooled by a water-cooled radiator, and the need for an air plume within the oven volume is obviated with suitable ports. Test methods can include injection of preheated gas into an oil sample, especially having standardized, predetermined level(s) of contaminant(s).

In general, the invention is useful in providing heating and cooling cycles in gas circulation ovens. It is especially useful in testing liquids for foaming at elevated temperatures.

Significantly, the present oven can heat and cool circulating gas, and hence, contained foam tester sample containers, rapidly, and accordingly, another major step forward is made in the art, in particular as pertains to that of foam testing of liquids. Many if not all of the aforementioned problems in the art are addressed, and much if not all of the same is ameliorated or overcome. Preferred plumeless foam tester embodiments of the invention are highly developed for simple, efficient operation. The foam tester may be employed to operate sample testing cycles without the removal of samples from the tester between tests and with high efficiency suitable for high volume applications in the modern testing laboratory. Cooling is most efficiently provided. Ease of operation is significantly enhanced.

Numerous further advantages attend the invention.

DRAWINGS IN BRIEF

The drawings form part of the present specification. With respect to the drawings, not necessarily drawn to scale and with like numerals referring to like features, note the following:

ILLUSTRATIVE DETAIL

Figure 1:
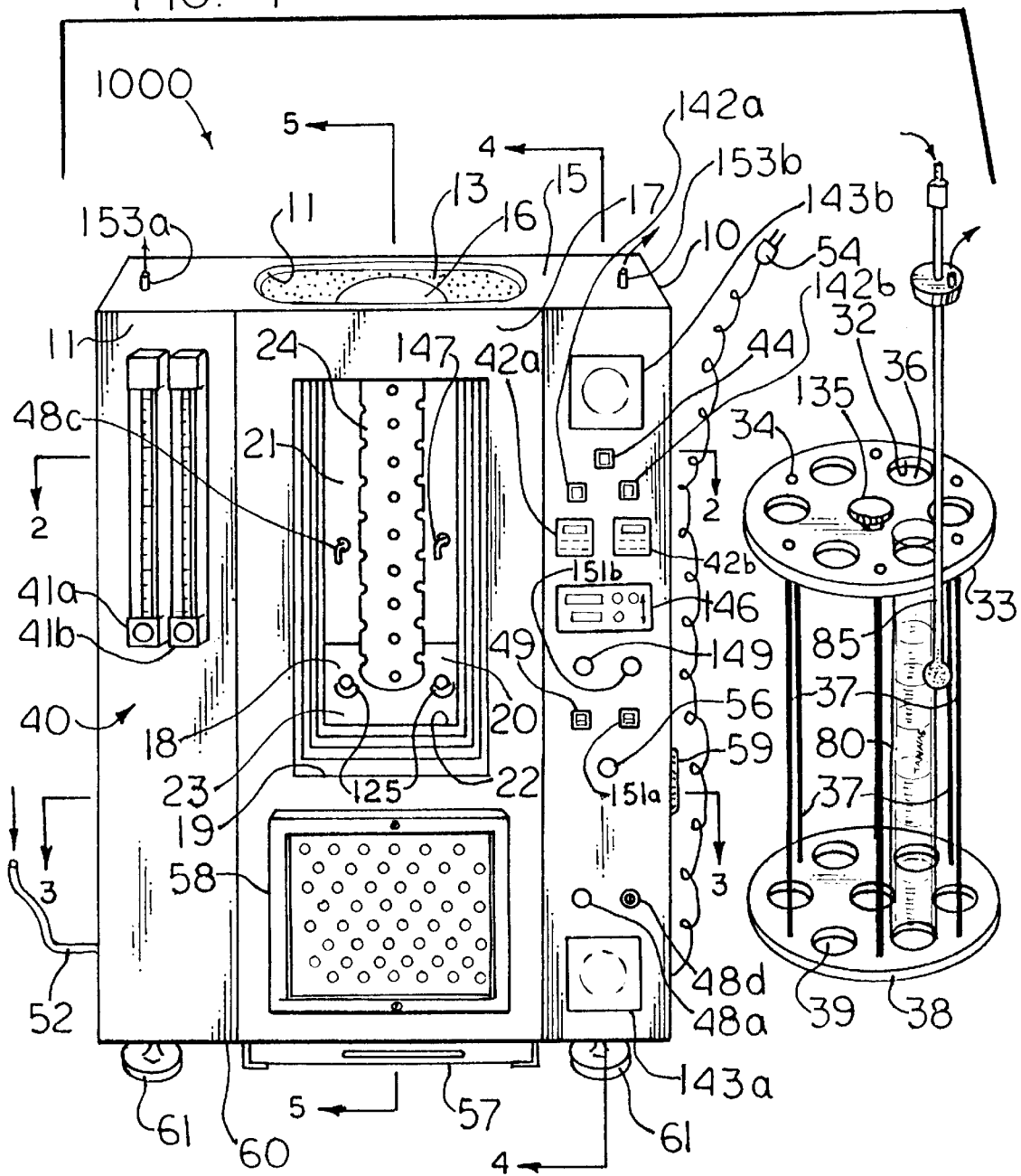
FIG. 1 is a front view of an oven of the invention, embodied as a foam tester device, with its carousel removed and shown alongside the cabinet.
Figure 2:
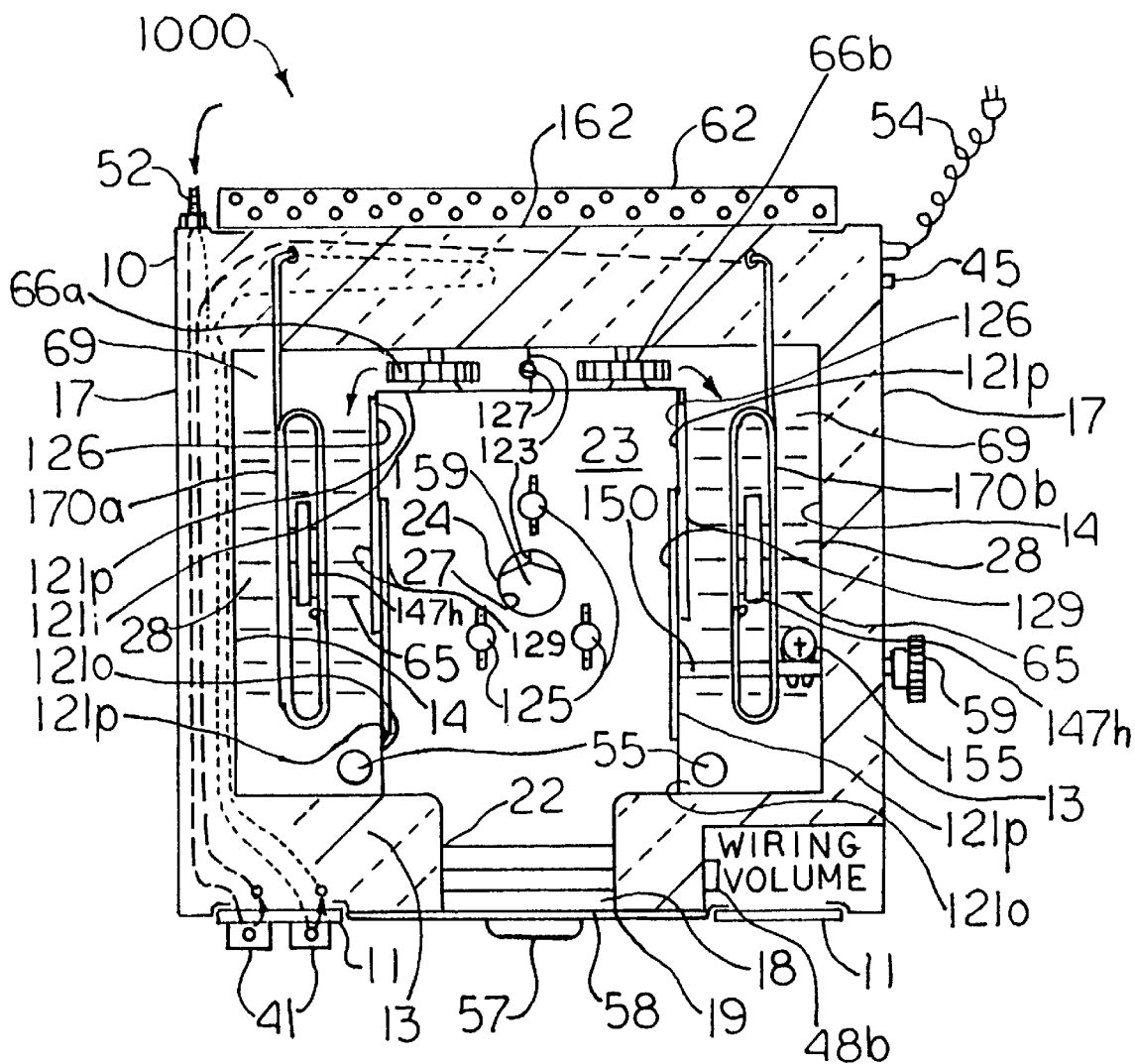
FIG. 2 is a top, cut-away view of the cabinet part, i.e., without carousel, of the device of FIG. 1, taken along 2—2.
Figure 3:
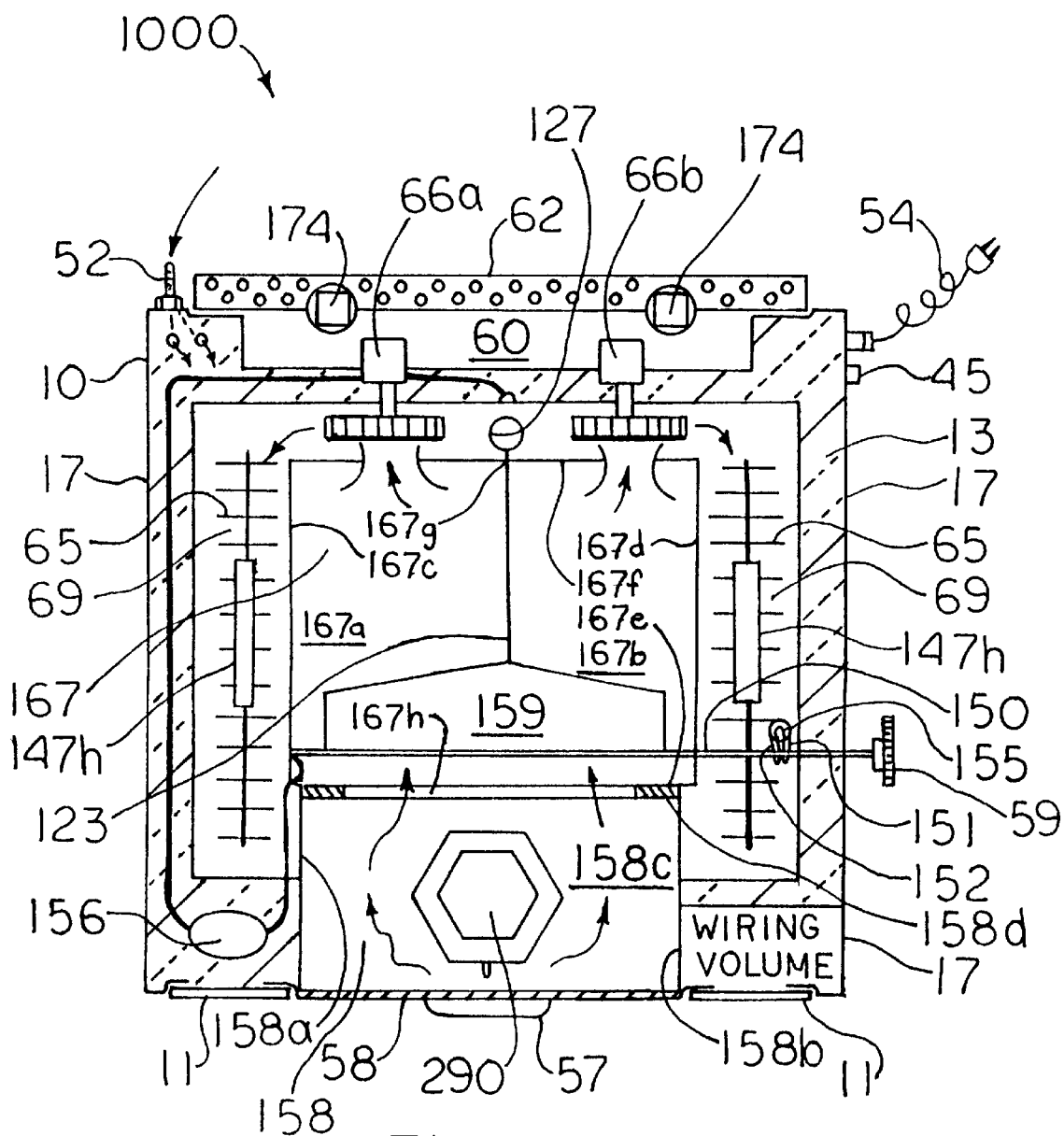
FIG. 3 is a top, cut-away view of the cabinet part of the device of FIG. 1, taken along 3—3.

The invention can be further understood by reference to the present detail, which may be read in conjunction with the accompanying drawings. The same is to be taken in an illustrative and not necessarily limiting sense.

The specification of the aforementioned patent application of Selby et al., Ser. No. 08/782822, is incorporated herein by reference.

The oven of the invention is a gas, especially air, bath. Preferably, ambient pressure is employed, which may include a slight overpressure wrought by intake blower(s) and/or a slight underpressure wrought by exhaust blower(s).

In reference to FIGS. 1–5, cabinet oven 1000 is embodied as a foam tester. As in the foam tester of the '822 application, in general, the foam tester 1000 of the present invention can be equipped with similarly operating features, as follows:

| Feature Identity | Number |
|---|---|
| Housing, cabinet | 10 |
| Top outside, e.g., 3/64- to 1/16-inch metal such as Al, steel, to include stainless steel (preferred) | 11 |
| Insulation, e.g., CERWOOL ceramic fiber, or a high-temperature glass fiber | 13 |
| Inside wall, e.g., 3/64- to 1/16-inch metal such as aluminum (Al), steel, to include stainless steel | 14 |
| Cabinet part top | 15 |
| Top access opening, e.g., an about 10-inch diameter hole | 16 |
| Cabinet outside wall, e.g., 3/64- to 1/16-inch metal such as Al, steel, to include stainless steel (preferred) | 17 |
| Tempered glass window, e.g., with four panes | 18 |
| Outside window gasket | 19 |
| Oven volume | 20 |
| Oven volume rear wall | 21 |
| Inside window gasket | 22 |
| Oven floor, e.g., Al sheet | 23 |
| Perforate circulation stack or air plume, e.g., Al, steel | 24 |
| Floor drain, e.g., as hole for air plume in oven floor | 27 |
| Side channels, for heating elements and so forth | 28 |
| Insertable carousel, member to hold sample container(s) | 30 |
| Outside, top, e.g., 1/4-inch thick KYDEX plastic layer, or other heat-resistant material | 31 |
| Insulative core, e.g., melamine, or 5/8-inch heat-resistant foam | 32 |
| Lower layer, e.g., Al with TEFLON polytetrafluoroethylene mechanically or adhesively fastened thereto, or a heat-resistant phenolic laminate | 33 |
| Fasteners, e.g., six nut and bolt type | 34 |
| Sample cylinder holes, e.g., six | 36 |
| Support rods, e.g., six TP314/304L ASTM A269 stainless steel, or Al | 37 |
| Carousel base, e.g., Al with TEFLON polytetrafluoroethylene mechanically or adhesively fastened thereto, or a heat-resistant phenolic laminate | 38 |

-continued

| Feature Identity | Number |
|---|---|
| Sample cylinder cups in carousel base, e.g., six | 39 |
| Front panel area | 40 |
| Air flow gages, e.g., Gilmont 150 mm GF-5531-2217 ball type | 41 |
| Main on/off switch | 44 |
| Main fuse | 45 |
| High-temperature (T) cut-out system indicator panel light | 48a |
| High-T cut-out control device, e.g., a WATLOW-92 unit with manual reset feature | 48b |
| Automatic oven volume heater heating on/off switch | 49 |
| Inlet for providing air or other gas for sample foaming | 52 |
| Electric supply cord, e.g., Carol 12/3 type SJOW-A (UL) 90-degree C., P-123-70-MSHA, CSA type 90-degree C., FT2 | 54 |
| Oven lights, e.g., two | 55 |
| Cabinet bottom, e.g., 1/8-inch thick painted steel | 60 |
| Screw-type, height-adjustable feet, e.g., four (in corners) | 61 |
| Lower back access panel, e.g., perforated aluminum (Al) | 62 |
| Heater, e.g., dual - electric resistance finned strip type | 65 |
| Positive pressure plenum, including side channels | 69 |
| Sample container,. e.g., 1000-mL graduated cylinder type | 80 |
| Bubbling wand assembly for generating foam in test sample | 85. |

Figure 4:
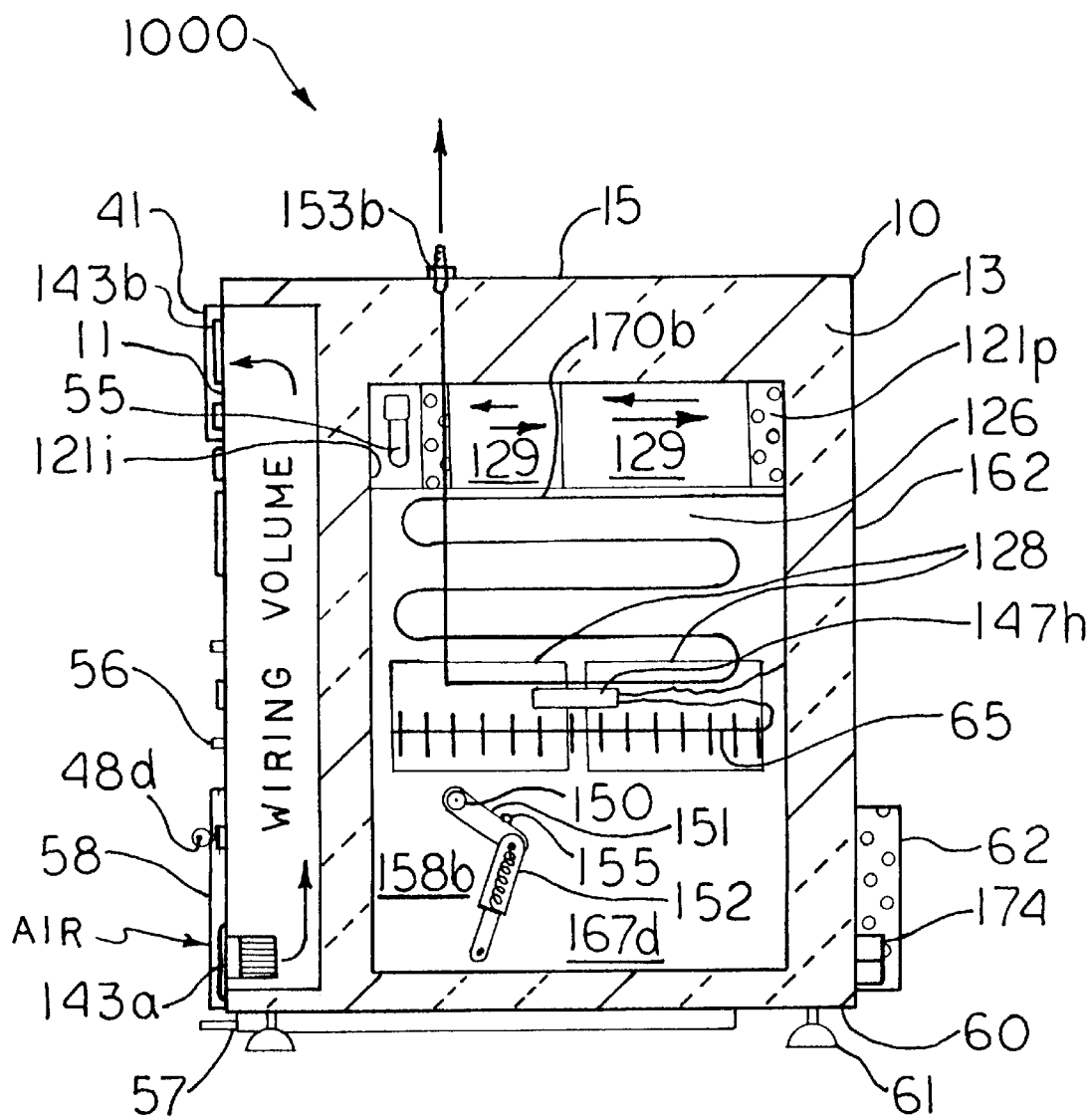
FIG. 4 is a side, cut-away view of the cabinet part of the device of FIG. 1, taken along 4—4.
Figure 5:
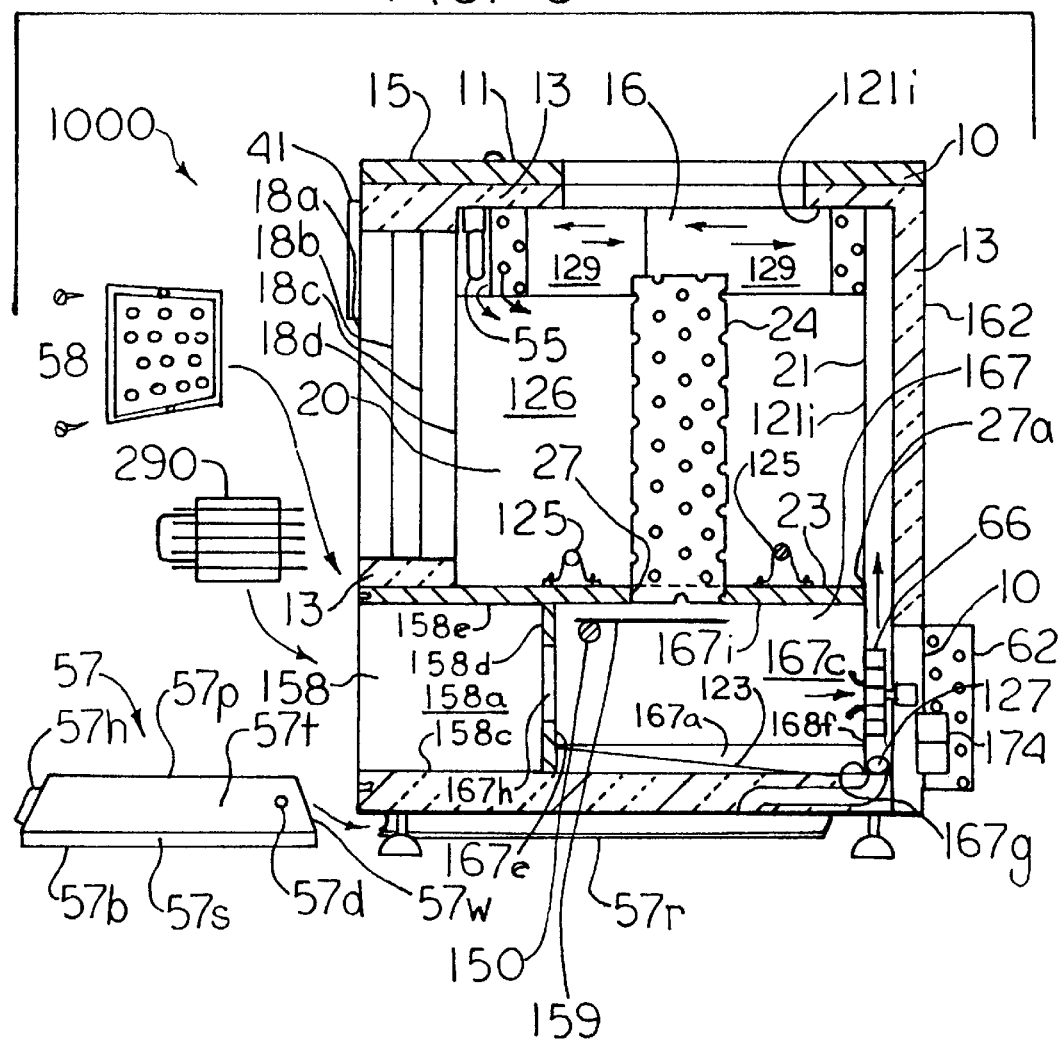
FIG. 5 is a partially exploded and side, cut-away view of the cabinet part of the device of FIG. 1, taken along 5—5.

The foam tester 1000 also can include features such as the following:

The cabinet 10 can also hold drain tray assembly 57. The assembly 57, for example, made of stainless steel, can be hollow and include pan bottom 57b, top drain hole 57d which may have a rubber gasket about its circumference, handle 57h, drain tray pan drawer support rails 57r mounted to the bottom 60 of the cabinet 10 on and into which the tray pan 57p may be slid in and out, and drain tray pan side 57s, top 57t (with the drain hole 57d therein through which liquids spilled inside the oven volume 20 may be drained) and width 57w (on the front of which the handle 57h is positioned). Also, protruding from the cabinet 10 on a side thereof is radially symmetric, scallop-edged handle 59, for example, of a hard plastic, which an operator can rotate so as to open and close internal door 159 for controlling the passageways employed in heating and cooling cycles; the handle 59 and door 159 are connected to rotatable axle 150, which can be mounted directly or indirectly to the housing 10 and equipped with an overcenter action to help insure that the door 159 stays either in closed or open position. Rather than being of aluminum, the lower back access panel 62 as well as the entire back panel can be stainless steel with louvers or punchouts, and it may be essentially flat with the entire cabinet deeper to accommodate suitable blowers and so forth. As shown in FIG. 4, the overcenter action can be provided by eccentric member 151 mounted to the axle 150, which member is pivotally connected about an upper end of elongate compression spring loaded member 152 pivotally mountable directly or indirectly about a lower end thereof to the housing 10; upon contact by the member 151 switch 155 such as a micro-switch or proximity switch can activate a circuit so that the heat on/off switch 49 cannot turn on heaters with the door 159 in its open, i.e., cooling air entry, position; the door 159 may have a "beaver tail" or V-shape feature to extend it as far as it can go into the V-shaped floor defined in part by groove 123 of negative pressure plenum 167. As well with the housing 10, gas egress ports 153a & 153b on housing top 15 provide independently monitored, heated gas, for example, air, for carrying by separate conduits (not illustrated) such as TYGON flexible plastic tubing to one or more, for example, three, bubbling wand assemblies 85.

The oven volume 20 can have thermocouple 48c, for example, mounted on the rear wall, which is part of the over-temperature and control system, and sends signals to the high-temperature cut-out control unit 48b, which shuts the heating down if the temperature becomes too high and signals the high-temperature cut-out system indicator panel light 48a, which lights up when the cut-out value is reached. Also, the volume 20 can be defined in part by imperforate wall sections 121i, for example, as provided by about 3/64-inch to 1/16-inch thick sheet aluminum, which can make up top, front and rear of the two side oven volume walls; open wall sections 121o, for example, two opposing about 2-inch wide by 6½-inch tall openings in the upper portions of the oven volume side walls, which basically are cut out sections to provide illumination and installation access for the lights 55, and air circulation orifices; and perforate wall sections 121p, for example, 3/64-inch to 1/16-inch thick sheet aluminum having about ¼-inch to ⅜-inch holes therein such as obtainable as PERFMETAL perforated metal sheets, which can make up the upper near-front (immediately rearward of the openings from open wall sections 121o) and upper rear side oven wall sections, each, say, of an about 4-inch width by 6½-inch height. Rolling ball carousel supports 125 can be mounted on the oven volume floor 23 and these can greatly facilitate rotation of the carousel 30. Also present are imperforate lower side walls 126, for example, of 3/64-inch to 1/16-inch thick sheet aluminum, behind which can be placed insulating tiles 128, for example, of ceramic, so as to ameliorate "hot spots" from the heaters 65. A gap 27a may be provided between the lower portion of the oven volume rear wall 21 and the oven volume floor 23 to provide an alternate passage for spilled liquids to drain. Thermocouple 147, for example, also mounted on the rear wall, which is part of a process temperature control system, and which sends its signals to a process control system device.

The carousel 30 can be equipped with handle 135, preferably which is centrally located, for example, a radially symmetric, scallop-edged of a hard plastic. This aids the operator not only in insertion and removal of the carousel 30 into and from the oven volume 20 but also in positioning the carousel 30 with the sample cylinders 80 therein for better sight alignment by facilitating rotation of the same in preparation for or during test runs.

The front panel area 40 also can include as the two gas flow gages 41, left side flow gage 41a (communicating with features 153a and 170a) and right side flow gage 41b (communicating with features 153b and 170b); first timer 42a and second timer 42b, for timing test runs and so forth; lower fan opening 143a with fan for drawing in outside air to cool inside instruments in the wiring volume, and upper vent 143b to permit hot air to exit from the wiring volume; in conjunction with the high-temperature cut-out control system, an over-temperature reset switch 48d, for example, one controlled by lock and key, working in conjunction with the WATLOW-92 unit 48b; "check blower" indicator light 56, which lights up when a preset low pressure differential between the positive and negative plenums 69 & 167, respectively, is reached so as to indicate if one of the blowers 66a or 66b is inoperative or operating at less than proper capacity; filter frame assembly 58 which holds a spun air filter between front and back imperforate metal sheets held by its edge frame, the same able to be fastened to the front panel 40, for example, by two screws; first timer starting push button switch 142a, which starts the timer 42a, and second timer starting push button switch 142b, which starts the timer 42b; process control system device 146, for example, a WATLOW-981 unit, which can control test run temperature and may monitor or control other test data. Heating cycle indicator light 149 lights up when the heating cycle on/off switch 49 is set at its "on" position when the heaters 65 are energized; and cooling cycle on/off switch 151a and cooling cycle indicator light 151b lights up when the cooling cycle on/off switch 151a is at its "on" position— and the internal door 159 is in its "open" position to permit cooling air to enter inside the hot oven.

Workings of the foam tester 1000 also include a thermostat (not illustrated) in the noted wiring volume so as to communicate to the system and the fan 43a an over-temperature situation in the wiring volume such that the fan 43a operates even though the main power switch 44 is in the "off" position; suitable circulation blowers 66a (left) & 66b (right), for example, Dayton model number 5M064A, 1/20-horsepower, 3000-rotations-per-minute, 115-volt, 60-Hertz, 2.9-ampere, class "B" impedance-protected pusher blowers, with the left pusher blower set to rotate in the counterclockwise direction when viewed from the front and the right pusher blower set to rotate in the opposite (clockwise) direction. Other speeds and types of blowers 66 may be employed. Negative pressure plenum floor drain crease 123 leads spilled liquids to hole 127 and associated conduit, which leads the spilled liquids to the drain tray pan drain hole 57d and the drain tray pan 57p for removal as may be needed. Imperforate sliding doors 129 such as of a metal, for example, aluminum, about the top, center of the side walls of the oven volume 20 are provided in pairs and can be adjusted to cover or uncover portions of the perforate wall sections 121p making up the upper near-front and upper rear side oven wall sections so as to regulate air flow and ameliorate temperature differentials in the oven volume 20 during heating cycle test runs. For example, on both sides of the oven volume 20, the sliding doors 129 can be adjusted to leave an about ¾-inch wide portion of the perforate wall sections 121p making up the upper near-front side oven wall sections, and an about ½-inch wide portion of the perforate wall sections 121p making up upper rear side oven wall sections, which can reduce temperature differentials in the oven volume 20 from an about 30-degree to 40-degree Fahrenheit value as can be found with the foam tester of the '822 application to a maximum of an about 6-degree to 7-degree Fahrenheit value initially in a heating cycle, i.e., when "cold," to a mere about 3-degree to 4-degree Fahrenheit value when the foam tester 1000 operates later in the heating cycle, i.e., when the device is "warmed up." Thermocouples 147h may limit temperature of the heaters 65.

Further workings of the foam tester 1000 include cooling plenum 158 and special negative pressure plenum 167. The cooling plenum 158 such as made of metal, for example, aluminum, can be generally in the form of a cube or a rectangular boxlike interior bounded by side walls 158a (left) and 158b (right); floor 158c; rear wall 158d, which can be considered to be the other side of a part of negative pressure plenum front wall 167e and also contain the hole 167h; and top 158e, which can be considered to be the underside of a part of the oven floor 23. The negative pressure plenum 167 such as made of the same metal as the cooling plenum 158 can have its drain crease 123 in part defining its inverted house-shaped interior, which is bounded by slanting bottom walls 167a (left) and 167b (right), which may be considered to define a sort of "invert roof"; side walls 167c (left) and 167d (right); front wall 167e; rear wall 167f; gap 167g between the floor 167a and rear wall 167f, especially about the crease 123 so as to provide drainage to hole 127 for any spilled liquids; front wall hole 167h which can communicate with the cooling plenum 158 when the door 159 is opened—otherwise, when the door 159 is closed the hole 167h is sealed from the cooling plenum 158; and top 167i, which also can be considered to be the underside of a part of the oven floor 23. The venturis of the blowing motors 66 mate with the rear wall 167f equidistant from a vertical midline thereof which intersects the crease 123 and about central in each left and right section formed thereby. In operation, when the door 159 is closed, the foam tester 1000 is in its heating mode, and the gas such as air is sucked down through the air plume 24 into the negative pressure plenum 167 by the blowing motors 66; from thence, the gas is blown and thus flows to the positive pressure plenum 69, side channels 28, oven volume 20 and back down through the air plume 24. When the door 159 is opened, the foam tester 1000 is in its cooling mode, and a gas, preferably air, can be sucked by action of the motors 66 through the filter 58 into the cooling plenum 158 preferably so as to be cooled by cooling device 290, from thence to the negative pressure plenum 167, and thence to the positive pressure plenum 69 and the oven volume 20 with or without the carousel 30 and sample containers 80 to cool the same; an extended "beaver tail" door 159, shaped generally like a "home plate" in baseball, can cover the hole 27 to as much as about ninety to ninety-five percent of its total cross-sectional area, which is highly. effective in providing cooling air to the oven volume 20 and contents; exhaust of the cooling air which is forced into the oven volume 20 may be provided by removal of a sample container 80 from the carousel 30 or by an external vent emanating from the oven volume 20 to the surrounding atmosphere.

Notably also in the foam tester 1000, air or other gas for making foam in liquids in the sample containers 80 through use of the wands 85 is provided with two separate but equal systems of conduits: The air or other gas enters through conduit fitting 52 from pressure supplied by a pump or as from bottled gas, and the conduit is divided into two separate conduits (dashed lines - - - & dotted lines . . . ) inside the cabinet 10; the air or other gas passes therethrough and into respective flow gages 41a & 41b, and then into tempering conduits 170a & 170b in the side channels 28 above the-heaters 65 of the foam tester 1000, where the air or other gas is heated, and from thence it is directed to respective gas egress ports 153a & 153b on the housing top 15. Each side of this foam-producing gas system has a total of about six feet of ¼-inch copper tubing being provided as coiled tempering conduit lengths 170a or 170b. Thus, the conduits are the same lengths from features 52 to 153a & 153b to provide for more reproducible foam generation in testing. As well, the foam tester 1000 has cooling motors 174 for cooling the blowers 66, but the cooling motors 174 may be eliminated such as when self cooling blowers, for instance, totally enclosed fan cooled blowing motors, are employed for the blowing motors 66.

Any suitable cooling unit or type of cooling may be employed with the foam tester 1000. Thus, cooling units such as disclosed by the '822 application, or other cooling units, may be employed. Alternatively, ambient air may be employed without chilling, but chilling is preferred for faster cycle times unless a chilled ambient air is employed such as during winter, and the cooling unit may embrace the cooling device 290, which can be removably inserted or permanently installed in the cooling plenum 158.

Figure 6:
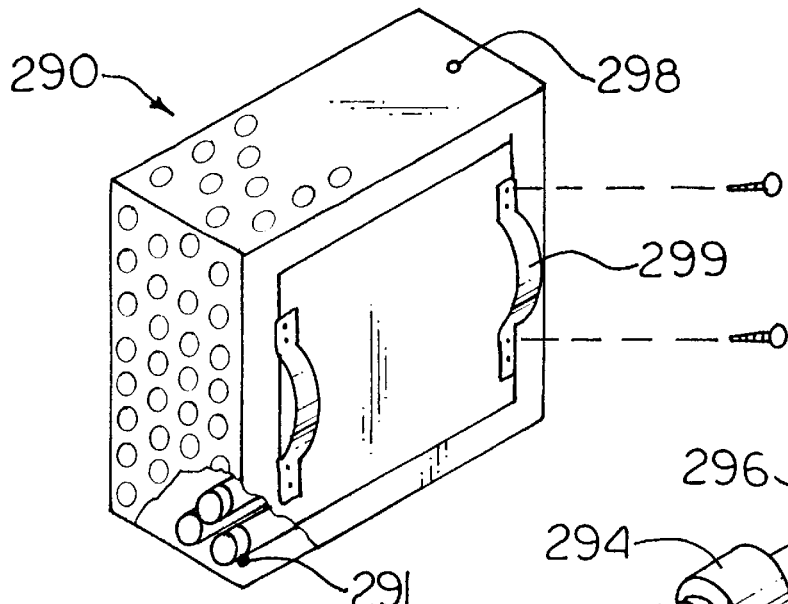
FIG. 6 is a perspective, partial cut-away view of a gel cooling package that may be employed in an oven of the invention.
Figure 7:
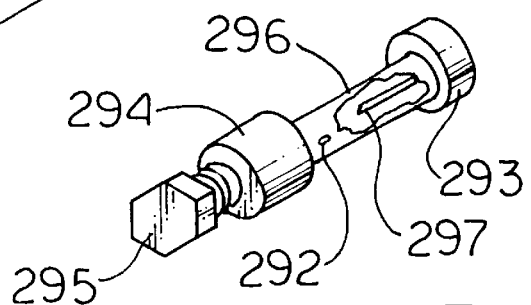
FIG. 7 is a perspective, partial cut-away view of a gel cooling cell employed in the gel cooling package of FIG. 6.

Advantageously, the cooling unit 290 employs gel cooling. For example, as depicted in FIGS. 6 & 7, gel tube assembly 291 may include copper tube 292 with a copper cap 293 on a first end of the tube 292 permanently attached such as by soldering, and with a copper part 294 permanently attached to a second end of the tube 292, which part 294 includes male threads accessible from the outside, i.e., the part 294 is a male to female adapter. Cap 295 with complementary female threads can seal the assembly 291 after freezer pack type gel 296 is inserted into the tube 292, and the gel 296 may be of any suitable variety, typically being a composition containing propylene glycol, water, a thickener such as corn starch, color and a bactericide, as available with units used in common picnic coolers. Optionally, cellular resilient material 297 may be employed for absorbing the force of expansion associated with freezing water. A plurality of such filled, capped tube assemblies 291 may be arranged in perforated housing 298, for example, of aluminum, which may have handles 299. The unit 290 with filled gel tube assembly(ies) 291 is cooled, usually to freezing, inserted into the plenum 158 of the oven 1000, and air or other carrying gas is circulated thereby to cool the same as it is introduced into other parts of the oven 1000.

Figure 8:
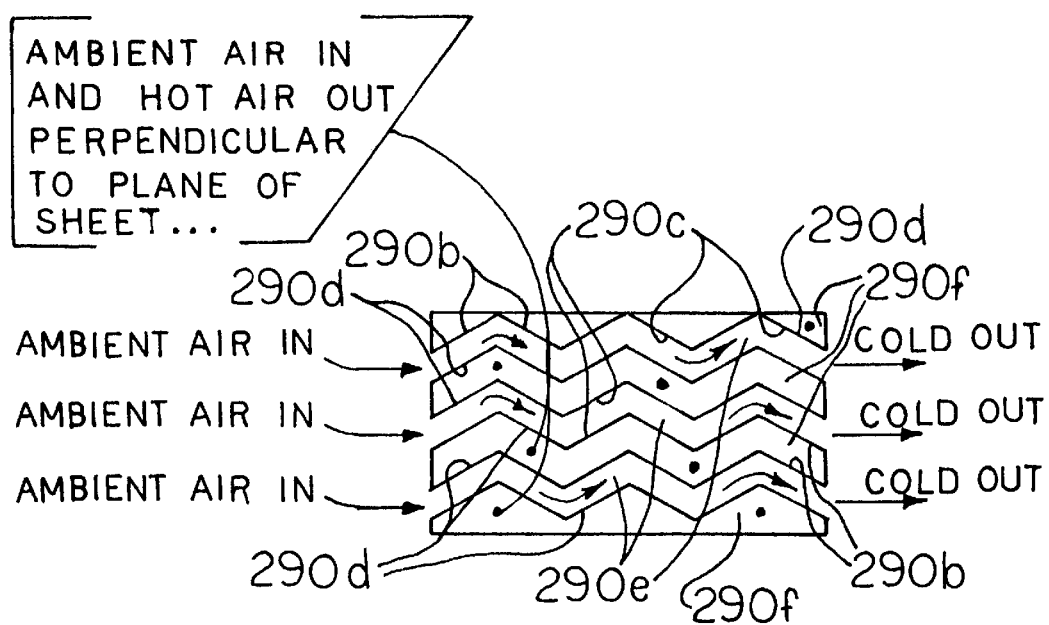
FIG. 8 is a plan view of a ferro-electric cooling device which may be employed in an oven of the invention.
Figure 9:
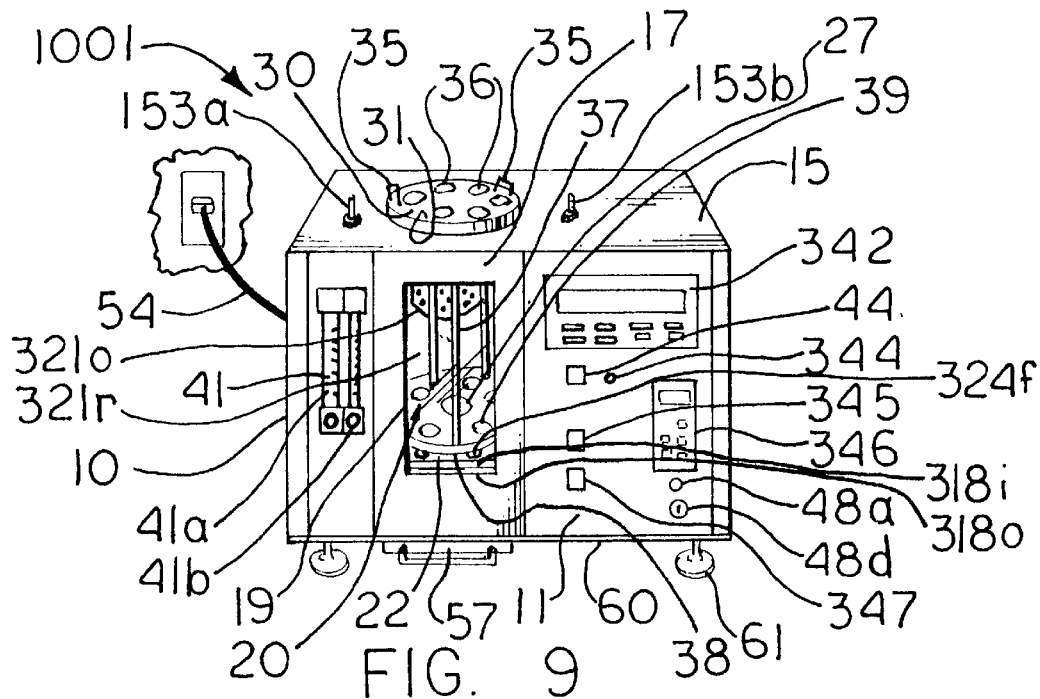
FIG. 9 is a front, perspective view of an oven of the invention, embodied as a plumeless foam tester device.
Figure 10:
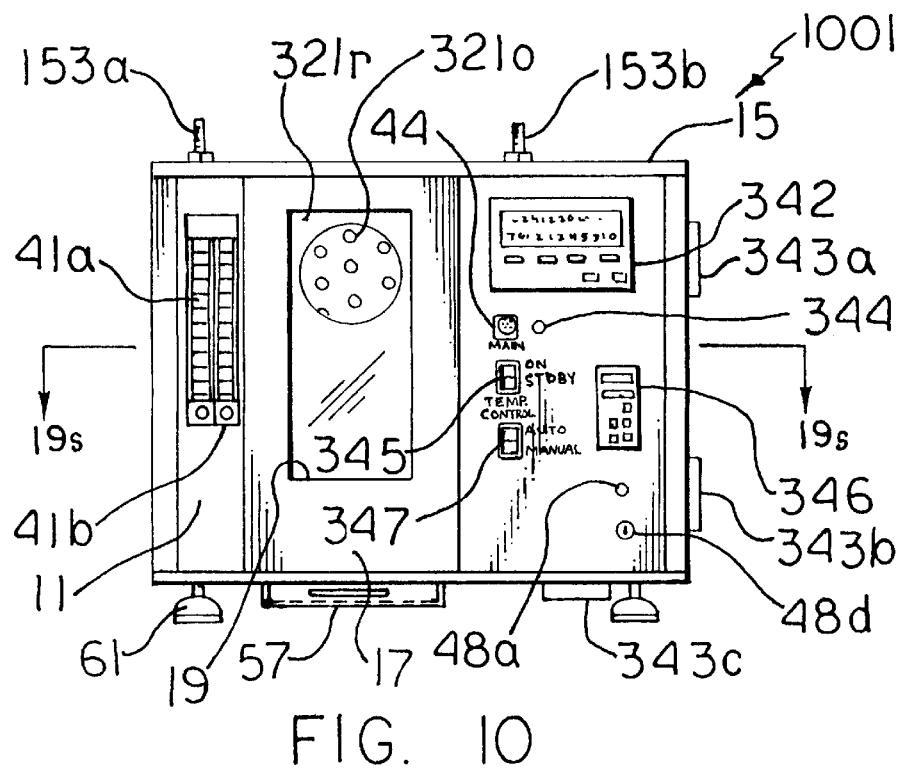
FIG. 10 is a front, elevational view of the device of FIG. 9, with its carousel removed.
Figure 11:
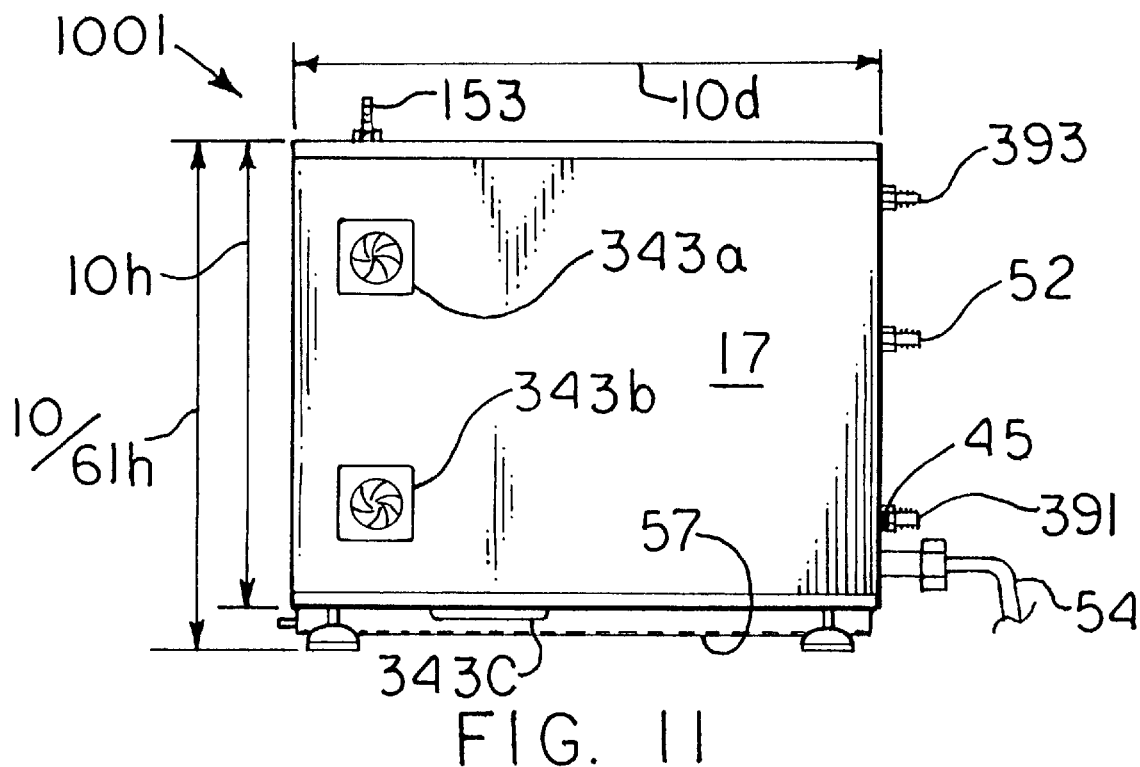
FIG. 11 is a right hand side, elevational view, from an operator's field of reference, of the device of FIG. 9.
Figure 12:
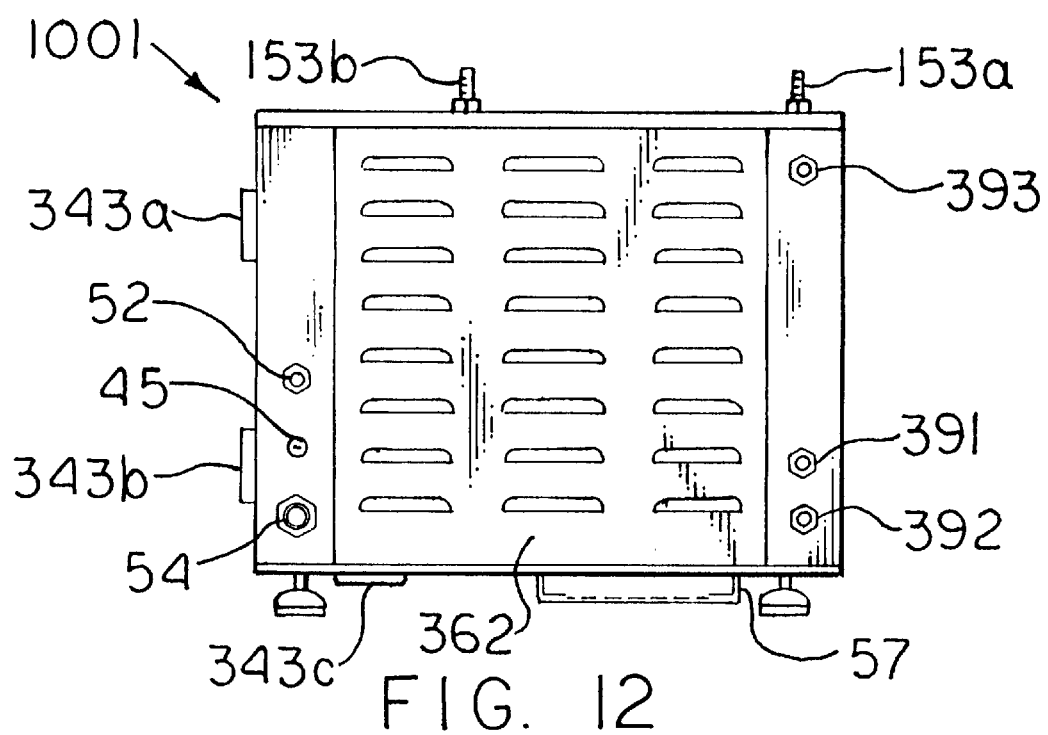
FIG. 12 is a rear, elevational view of the device of FIG. 9.
Figure 13:
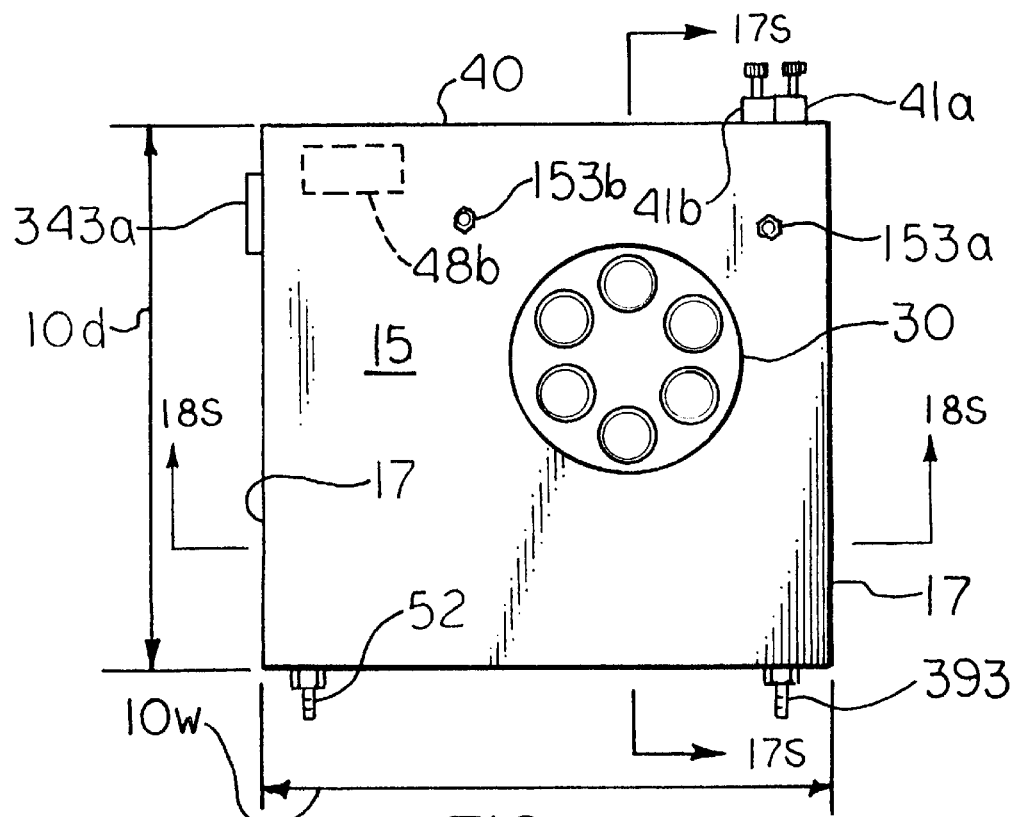
FIG. 13 is a top view of the device of FIG. 9.
Figure 14:
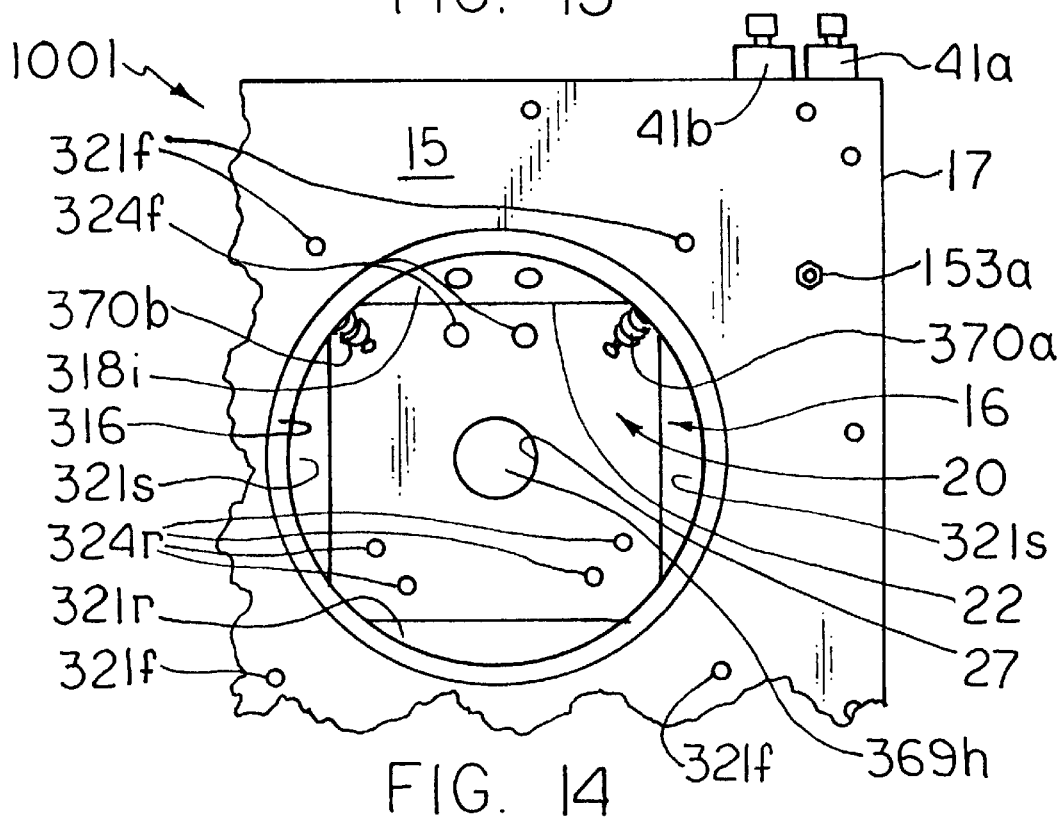
FIG. 14 is a top view of the device of FIG. 9, with its carousel removed.
Figure 15:
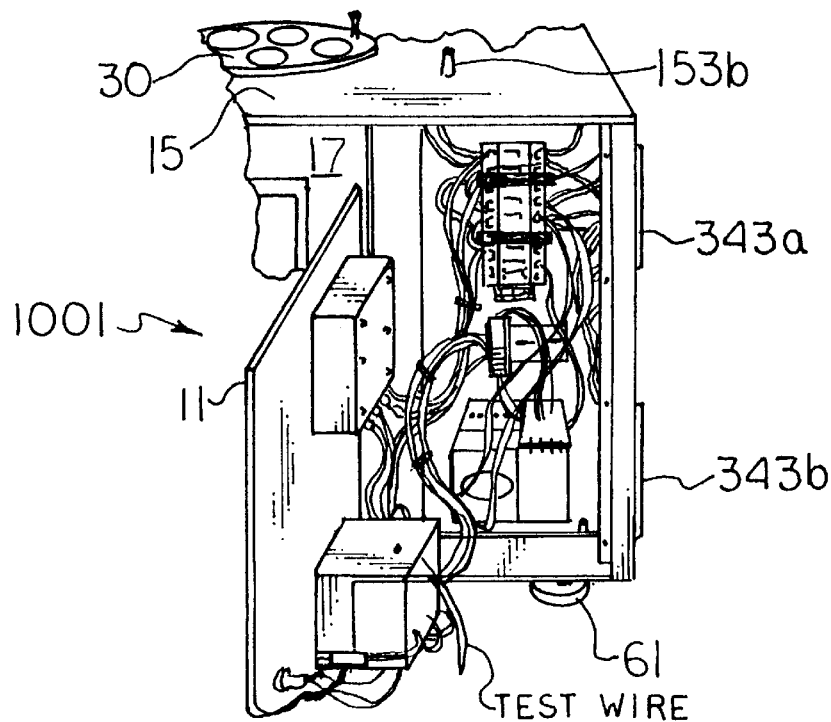
FIG. 15 is a front, perspective view of the device of FIG. 9, focusing upon its controlling wiring closet.
Figure 16:
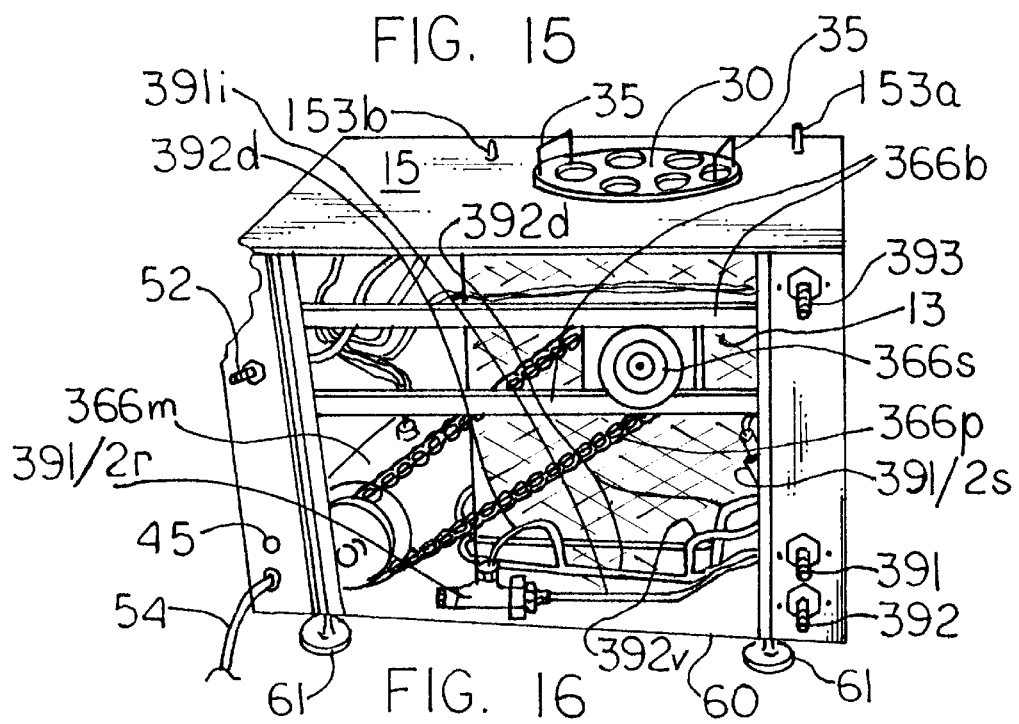
FIG. 16 is a rear, perspective view of the device of FIG. 9, with its rear panel removed.
Figure 17:
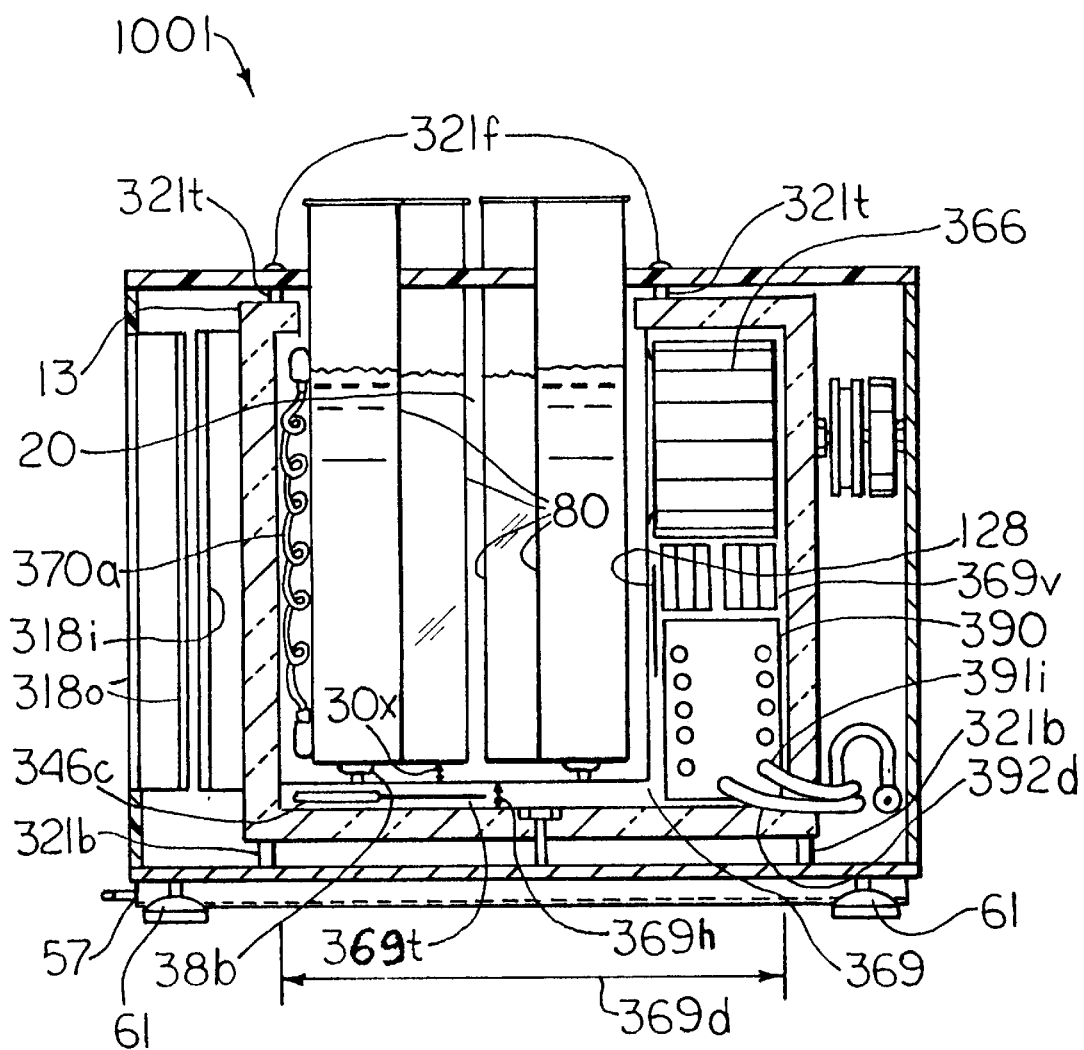
FIG. 17 is a side, partial sectional, plan view of the device of FIG. 9, with the section taken along 17s—17s shown in FIG. 13.
Figure 18:
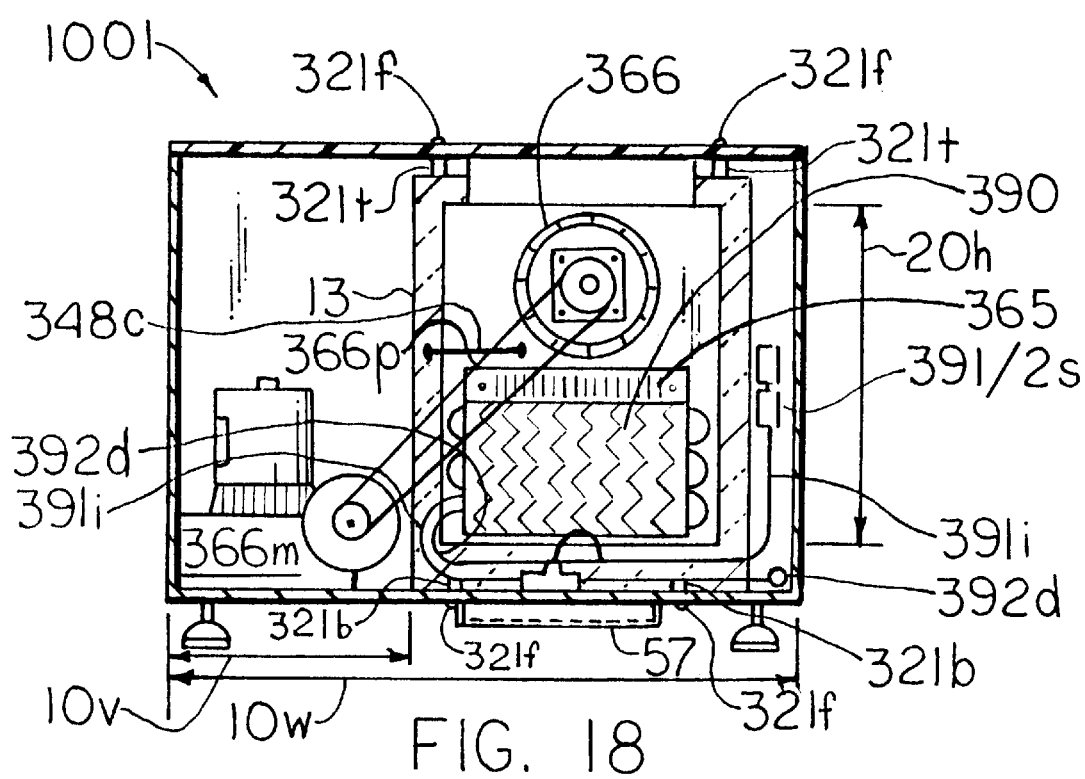
FIG. 18 is a rear, partial sectional, plan view of the device of FIG. 9, with the section taken along 18s—18s shown in FIG. 13.
Figure 19:
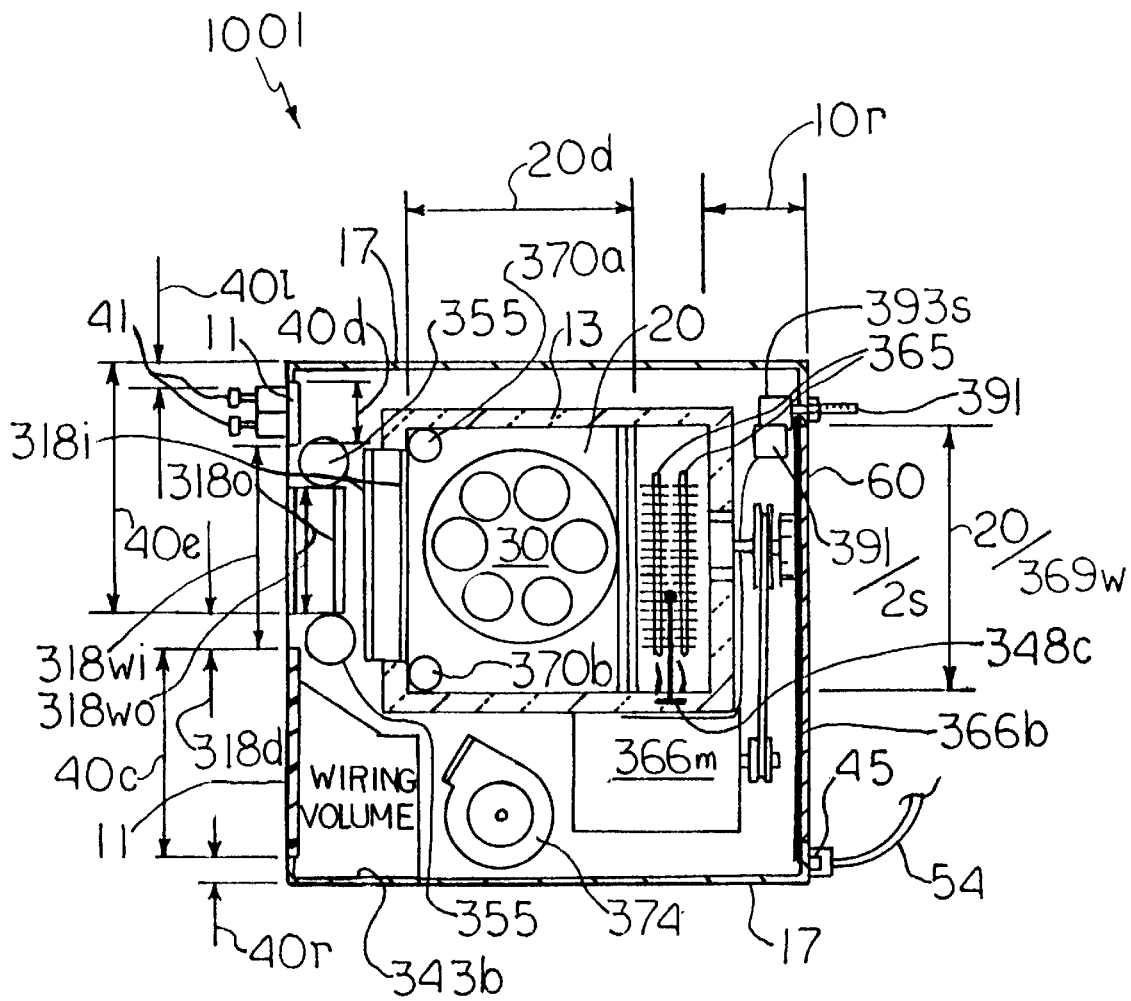
FIG. 19 is a top, partial sectional, plan view of the device of FIG. 9, with the section taken along 19s—19s shown in FIG. 10.
Figure 20:
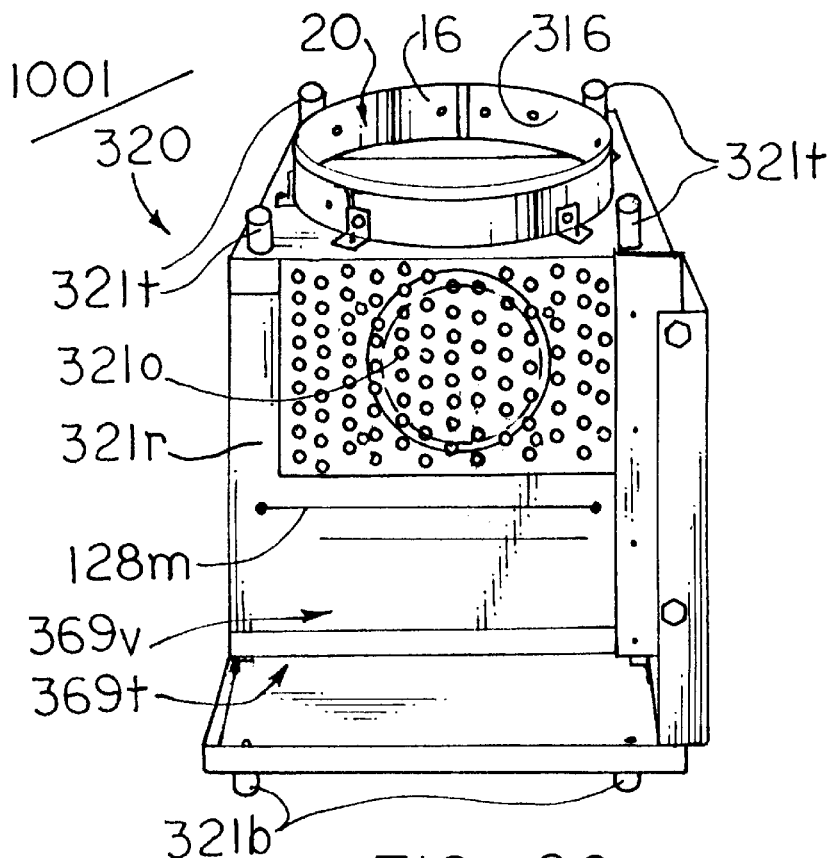
FIG. 20 is a rear, perspective view of the oven volume unit housing, in a state of partial assembly, of the device of FIG. 9.
Figure 21:
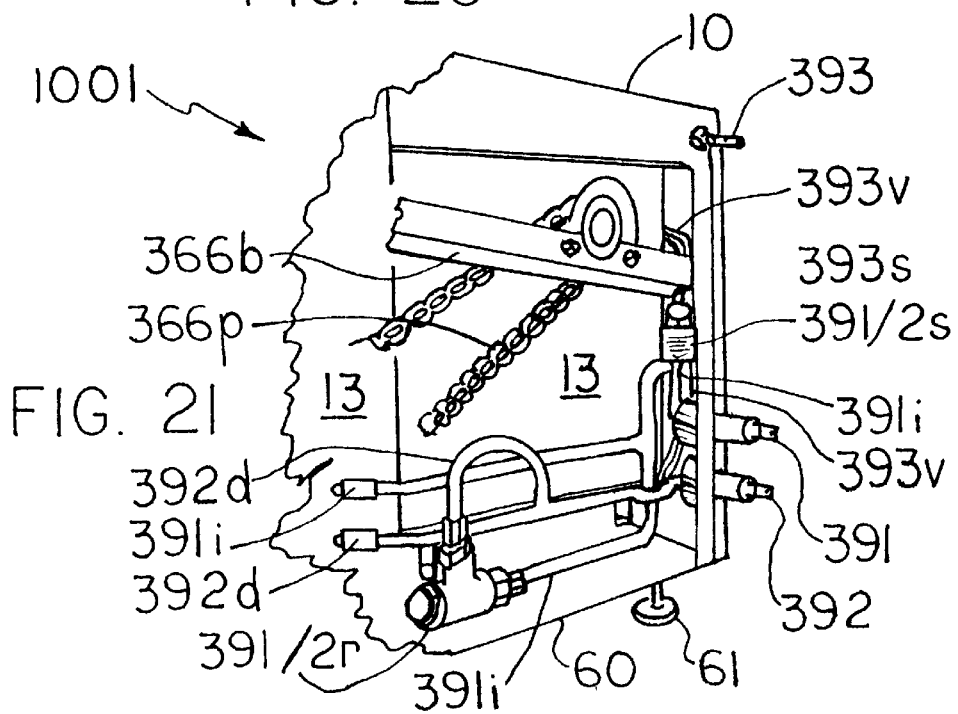
FIG. 21 is a rear, perspective view of the device of FIG. 9, with particular focus on some oven volume service features.
Figure 6:
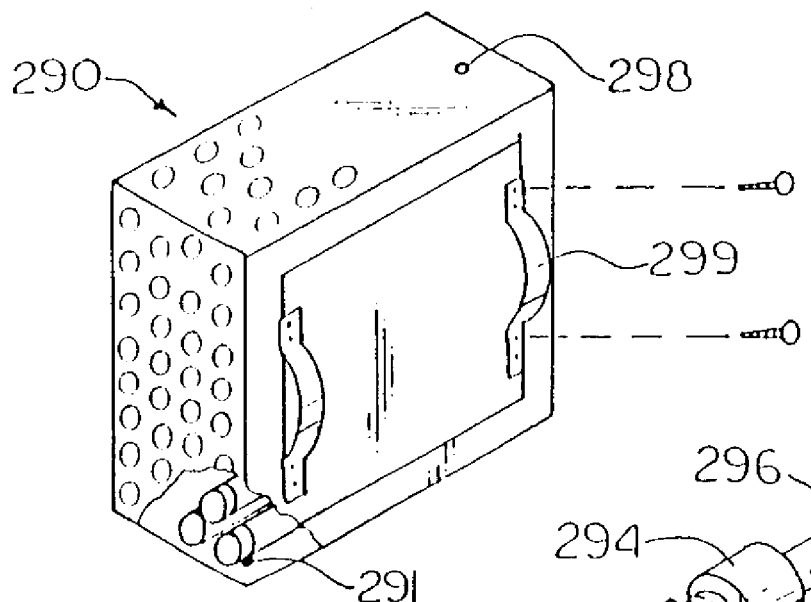
Figure 7:
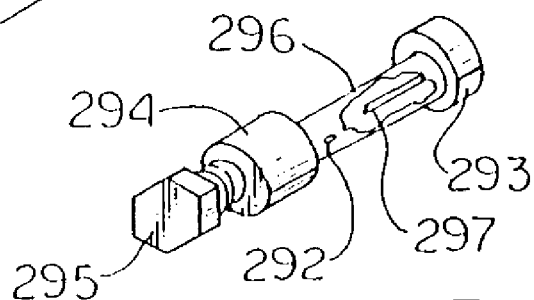
Figure 8:
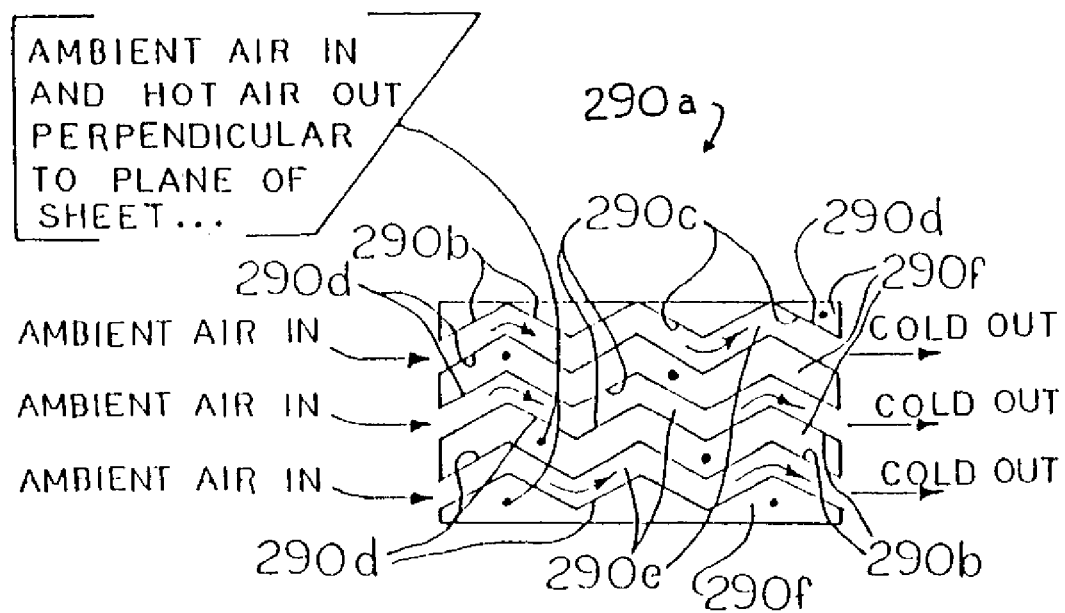

As another alternative, the cooling device 290 may be a solid state cooling unit such as so-called ferro-electric unit, which operates on the Peltier effect. For instance, as depicted in FIG. 8, alternate, solid-state cooling device 290a has Peltier effect chips 290b arranged in a suitable housing provided with electric power so that cold sides 290c of the chips 290b face each other and hot sides 290d face each other to form separate cold and hot channels 290e and 290f, respectively, with the cold channels 290e perpendicular to the hot channels 290f. The device can be set up so that air is drawn in through the cold channels 290e to be cooled in the plenum 158 for providing cool air to cool the appropriate parts of the oven 1000. Simultaneously, air is drawn across through the hot channels 290f to be expelled on a side of the oven 1000 where the same will not be drawn in the front, or where ever the intake is for the air to be cooled.

The foam tester 1000 is amenable to automation. For example, solenoids may provide communication between flow gage 41a and timer 42a and between flow gage 41b and timer 42b so as to work with a programmable device such as an electronic programmable logic controller or mechanical sequencer or combination of relays producing a circuit commonly referred to as relay logic.

Accessory features may be added, deleted or modified.

The oven of the invention is made to any suitable dimension. For example, the foam tester 1000 includes dimensions, in inches (")—which may be considered to be approximate—as follows:

| Feature Identity | Dimensions |
| --- | --- |
| Cabinet 10 | 21" wide × 21" deep × 25" tall |
| Cabinet 10 plus feet 61 | 21" wide × 21" deep × 26" to 27" tall |
| Window 18 | 5-3/4" wide × 13" tall |
| Window panes 18a & 18d | 1/4" thick |
| Window panes 18b & 18c | 1/8" thick |
| Oven volume 20 | 11-1/4" wide (top) to 10-3/4" (bottom) × 13-1/4" deep × 15-3/4" tall |
| Stainless st./Al plume 24 | 3/64" to 1/16" thick, 3" diameter × 14-1/2" tall |
| Side channels 28 | 1-3/4" wide × 13" deep × 15-3/4" tall |
| Carousel 30 | 15-15/16" diameter × 17-1/2" tall |
| Sample cylinder holes 36 | 2-5/8" diameter circular holes in top and lower layer, 2-1/2" holes in foam |
| Carousel support rods 37 | 3/8" diameter × 15" tall |
| Carousel base 38 | 15-15/16" diameter × 1/4" tall |
| Sample cylinder cups 39 | 2-9/16" diameter × 3/16" deep |
| Hollow drain tray pan 57p | 8" wide × 16" deep × 11/16" high, with 3/4" hole center 14-3/4" from front |
| Filter frame assembly 58 | 8-3/8" wide × 1/2" deep × 7-1/2" tall |
| Sliding doors 129 | Each 8" wide × 6-1/2" tall |

-continued

| Feature Identity | Dimensions |
|---|---|
| Cooling plenum 158 | 8" wide × 8" deep × 8" tall |
| Lower pressure plenum 167 | 12-1/2" wide × 5-3/4" deep × 5" tall, in general, at sides; 5-3/4" tall at front center & 6" tall at rear center. |

In reference to FIGS. 9–21, cabinet oven 1001 is embodied as a plumeless foam tester.

In general, the plumeless foam tester 1001 does not have an air plume such as found in the foam tester 1000 (24); however, the device 1001 includes a cooling volume apart from the oven volume for containing coolant material. Nonetheless, the cooling volume of the plumeless foam tester 1001 is not physically closed off from the oven volume when the device is in heating mode as in the foam tester 1000; rather, the plumeless foam tester 1001 has a drainable liquid cooling system installed in a gas-conducting passageway which leads to and is in communication with the oven volume. The same passageway or volume, with the cooling liquid drained from the cooling system, serves as a heating passageway when the plumeless foam tester 1001 is in heating mode.

As in the foam tester of the '822 application, in general, the plumeless foam tester 1001 of the present invention can be equipped with analogous features, as follows:

| Feature Identity | Number |
|---|---|
| Cabinet housing | 10 |
| Outside wall, e.g., of 1/4-inch thick KYDEX thermoplastic | 11 |
| Insulation around oven volume, e.g., of woven glass fiber, one inch in thickness with an aluminuin foil skin | 13 |
| Inside oven volume wall, e.g., of aluminuin sheet metal | 14 |
| Cabinet top, e.g., of L-50 fiber-based epoxy composite (Polycomposites) some 1/4-inch thick | 15 |
| Top access opening, about ten inches in diameter | 16 |
| Cabinet outside wall, e.g., of stainless steel | 17 |
| Outside window gasket | 19 |
| Oven volume | 20 |
| Inside window gasket | 22 |
| Center hole in oven volume floor to lower plenum | 27 |
| Insertable sample carousel | 30 |
| Carousel outside, top, e.g., of the 1/4-inch L-50 material, with insulative core, and lower, inside layer of ULTEM-1000 polyetherimide resin with a 332-degree Fahrenheit rating | 31 |
| Handles, e.g., two, each of stainless steel | 35 |
| Sample cylinder holes, e.g., six | 36 |
| Support rods, e.g., six, each of stainless steel | 37 |
| Carousel base, e.g., of aluminum with large center hole communicating with large center hole in oven floor from lower plenum (being further present underneath the base, however, for spinning the carousel on the oven floor, a low profile ball bearing turn table 38b, e.g., a 9-inch round McMaster-Carr Supply model-6031K21 turn table with a 4-1/2 - inch center hole, carbon-steel ball bearings in a track near the outside perimeter of the turn table, and a 750-pound load capacity rating) | 38 |
| Sample container receiving cups in base, e.g., six | 39 |
| Front panel area | 40 |
| Gas, e.g., air, flow gages, e.g., Gilmont 150-mm ball type | 41 |
| Left hand gas, e.g., air, system gage | 41a |
| Right hand gas, e.g., air, system gage | 41b |
| Main on/off switch | 44 |
| Main fuse (rear mounted) | 45 |
| High temperature cut out light | 48a |
| High temperature cut out control device, e.g., a WATLOW-92 unit | 48b |
| Overtemperature key reset switch | 48d |
| Inlet for providing air or other gas for sample foaming | 52 |
| Electric supply cord | 54 |
| Cabinet bottom, e.g., 1/4-inch thick painted steel | 60 |
| Cabinet feet, e.g., four height-adjustable screw-type | 61. |

As in the foam tester 1000 hereof, in general, the plumeless foam tester 1000 can be equipped with like features, as follows:

| Feature Identity | Number |
|---|---|
| Drain tray assembly | 57 |
| Heat-insulating tile | 128 |
| Heat-insulating tile installation line mark (FIG. 20) | 128m |
| Gas egress ports for heated gas, e.g., air, for foaming | 153 |
| Independent left hand side gas system egress port | 153a |
| Independent right hand side gas system egress port | 153b. |

The plumeless foam tester 1001 also can include features such as the following:

Multi-pane, heat-insulating, wide-range-of-view window 318 includes wider inner window 318i, for example, with two panes, and narrower outer window 318o, for example, with two panes. Silicone sealant/adhesive is used for each pane. Air is present between the panes. A capillary tube extends from within the confined volume to atmosphere in between each pane to relieve heat induced pressure but prevent moisture form being inhaled upon cooling.

In general, oven volume housing 320 defines the oven volume 20, which is composed of oven volume cage walls, for example, of aluminum sheet metal: rear wall 321r, two imperforate side walls 321s, and top 321t. The inside window 318i completes the definition of the oven volume 20, generally speaking. The rear wall 321r is imperforate, save blower intake opening 321o with grill. The top wall 321t is also imperforate, save the carousel access hole 16. Advantageously, defining the carousel access hole 16 can be heat-insulative, low-friction material 316, for example, such as of suitable plastic, e.g., of Teflon polytetrafluoroethylene. Oven volume floor 23, for example, made of aluminum, includes the center hole 27; front circulation holes 324f, for example, two in number, each with an about ⅞-inch diameter placed (on center) about one inch from the inside boundary of the inner window 318i and about 1 9/16 inches from the nearest side wall 321s; and rear circulation holes 324r, for example, four in number and all with an about ⅞-inch diameter, one set of two of which (e.g., left hand side set) having a first hole placed (on center) about 1 9/16 inches from the inside boundary of the rear wall 321r and about 2 9/16 inches from the nearest side wall 321s and a second hole placed (on center) about 2 9/16 inches from the inside boundary of the rear wall 321r, and the other set of which (e.g., right hand side set) being a mirror image thereof. Each of the holes 27, 324f & 324r are open to and in communication with positive pressure plenum 369. The oven volume housing 320 is connected to, but set off from, the cabinet housing 10 by sets of set-off post fasteners 321f which secure the same through a series of heat-insulating set-off posts 321b (bottom) and 321t (top). Lights 355, shining through the inner window 318i, are placed within the cabinet 10 but outside the oven volume 20 so as to illuminate the same.

The positive pressure plenum 369 can have, in general, portions including special lower, narrow-height, transverse plenum 369t and special rear, vertical plenum 369v. The holes 27, 324f & 324r to the oven volume 20 preferably are in direct communication with the lower plenum 369t, and the lower plenum 369t is open to and in communication with the rear plenum 369v. Preferably, in general, the interior of the lower plenum 369t is void of solid features, but the interior of the rear plenum 369v contains gas/air heater 365 and gas/air cooling radiator 390.

The heater 365 is any suitable for the job. Advantageously, however, the heater 365 is composed of a plurality of heaters, for example, two, one with a 725-watt element, e.g., a Vulcan model #OSF1510-725B) and the other with a 475-watt heater element, e.g., a Vulcan model #OSF1510-475B), which, together, are highly effective in and adapted to commonly encountered 20-amp electric service. The heater 365 can be mounted below circulation blower 366 and above the radiator 390.

The blower 366 is a high-volume gas/air blower, preferably of the squirrel-cage variety. For example, a 500-cubic feet per minute (cfm) to 700-cfm capacity squirrel-cage arrangement, e.g., a model #1-1548 squirrel cage blower supplied by York Electric, can be provided as the blower 366. The blower 366 can be mounted on brackets 366b through its bearing housing, the bearings of which, for example, can be AMI bearings rated to a 372-degree F. temperature. The blower can be driven by electric motor 366m which, through heat-resistant pulley 366p, for example, such as an adjustable Acculink V-groove fiber-reinforced rubber variety having a 280-degree F. rating, drives heat-insulative blower shaft 366s, for example, of G-11 fiber-epoxy material. The intake for the blower 366 is the gas/air passing through the blower intake opening 321o from the oven volume 20, and, from the blower 366, the gas/air is forced into the rear plenum 369v, from there to the lower plenum 369t, and from there to the oven volume 20. The presence of the heater 365 and radiator 390 as well as fins included therewith causes increased turbulence in the plenum 369 and, in conjunction with the entry holes 27, 324f & 324r and impetus of the high-volume blower 366 itself, assists in an even temperature distribution in the oven volume 20 through dynamic convection without a plume. Be that as it may, it has been found that with the high-volume, turbulent flow of air in the oven volume 20, occasioned from the features in the device 1001, a strictly even or uniform value of temperature in the oven volume 20 is not critical for obtaining highly reproducible foam test data in the device 1001.

The radiator is any suitable for the job. Advantageously, however, the radiator 390 is a liquid-cooled radiator, from which the cooling liquid can be drained when the device 1001 is in heating mode and through which the cooling liquid can be pumped when the device 1001 is in cooling mode. For example, the radiator 390 can be a water-cooled unit, e.g., a Peerless model #3660-0-12 unit, with metal cooling fins which contact the gas/air passing thereby in the plenum 369. Such a radiator may be in a radiator system which can include cooling water ingress port 391, water exit port 392, and water vapor escape port 393, each, for instance, made of a suitable heat-insulating material such as of heat-insulative plastic, for example, of Kynar nylon composite, which has a 285-degree Fahrenheit (F.) rating. In conjunction with the radiator 390 and ports 391, 392 & 393, are water input lines 391i, for example, of copper tubing; water drain lines 392d, for example, of copper tubing; pressure relief valve 391/2r, e.g., set to a 125-p.s.i. (pounds per square inch) value; and water vapor escape line 393v, for example, of copper tubing. The system is controlled by two solenoids, a first one 391/2s, which controls liquid water flow lines, and a second one 393s, which controls the vapor escape line. The solenoids are programmed to be either the first open and the second closed (cooling mode) with water, for example, from the tap, entering the port 391 cool and exiting the port 392 carrying off heat, or the first closed and the second open (heating mode) with draining of the radiator 390 as well as escape of any left over water accelerated and facilitated through the open vent port 393.

Separate but equal gas/air tempering lines include tempering coils 370a & 370b, for example, of $3/16$-inch inside diameter and ¼-inch outside diameter copper tubing coiled helically seven times or so with a helical radius of about two inches for a distance of about a foot more or less, inside the oven volume 20. This arrangement is most efficient in the tempering of the gas, for example, air, which enters through the coupling 52, travels through separate lines, and, so separated, passes through the insulation 13 and side wall 321s to the coils 370a or 370b to be heated, and then, so tempered, passes out the side walls 321s and to the proper gas egress port 153a or 153b. The tempered gas/air is employed to generate foam in the sample in the sample container 80.

Front gages and signal lights can include, in addition to the main switch 44, the high temperature cut-out light 48a and the overtemperature cut-out key reset switch 48d, for example, display-transmission module 342, e.g., an ATM-20 unit (NAIS), for providing visual messages to the operator as well as providing the input signals to a programmable logic controller (PLC); main power indicator light 344; sequence selector switch 345, which permits the operator to select between preprogrammed test runs; temperature control unit 346, e.g., a WATLOW-988 device; and cooling switch 347, which permits the operator to turn on the cooling function. In the device 1001, the main switch 44 controls electrical power to the components of the unit, i.e., the module 342, lights 355, blower 366, and so forth. A wiring volume, in addition to the high temperature control 48b, contains microprocessors and other regulatory instrumentation, and it is cooled during use by warm air exiting upper side cooling vent 343a and being drawn into the wiring volume by a blower motor through lower side cooling vent 343b. Internal cabinet components are cooled through air entering vent 343c and being forced by blower motor 374 onto such items as the oven volume insulation 13, lights 355, motor 366m and so forth, and from thence out louvered, stainless steel back panel 362.

Resistive temperature device (RTD) couple 346c, for example, a WATLOW 4-inch RTD, which can be located in the front of the lower plenum 369t, provides input to the temperature controller 346 for effective temperature control of the oven volume bath. Thermocouple 348c, located in the upper portion of the rear plenum 369v, generally between the heater 365 and blower 366, provides the input for the temperature cut-out control unit 48b.

Most notably, with the oven volume 20, hole 27, 324f & 324r, heater 365, blower 366, plenum 369, radiator 390 and so forth arrangement, heating and cooling cycle times in the device 1001 can be quite astoundingly fast. For example, heating cycle (24-degree Celsius (C.) to 150-degree C. oven volume temperature) times as short as fourteen minutes, or less, and cooling cycle (150-degree C. to 10-degree C. oven volume temperature) times as short eighteen minutes, or less, have been attained with regularity. This compares most favorably with any foam tester device, to include even the device 1000, which has a relatively fast cycle time of about half an hour to heat and half an hour to cool, and is a definite practical improvement in kind over even the foam tester devices of Selby et al., Ser. No. 08/782822.

Moreover, with the aforesaid arrangement, the device 1001 can provide for a highly uniform heating and temperature distribution within the oven volume 20, notwithstanding the fact that the same need not be exactly uniform. For example, a heat and temperature distribution in the foam testing mode has been found to be at a 150±3-degree C. value, or better. This compares most favorably with the air plume containing foam tester devices, to include the device 1000. See, infra.

Advantageously, the device of the invention, especially, for example, the device 1001, is made to CE (European) standards.

Dimensions of the device 1001 may vary. Nevertheless, for example, the following dimensions, which may be considered to be approximate, can be found with the foam tester of FIGS. 9–21:

| Feature Number | Dimension |
| --- | --- |
| 10d (FIG. 13) | 24 inches (61 cm) |
| 10h (FIG. 11) | 18-1/2 inches (47 cm) |
| 10r (FIG. 19) | 3-3/4 inches (9-1/2 cm) |
| 10v (FIG. 18) | 8-1/4 inches (21 cm) |
| 10w (FIGS. 13 & 18) | 24 inches (61 cm) |
| 10/61h (FIG. 11) | 19-15/16 inches (50-1/2 cm) |
| 20d (FIG. 19) | 12 inches 30-1/2 cm) |
| 20h (FIG. 18) | 14-15/16 inches (38 cm) |
| 20/369w (FIG. 19) | 12 inches (30-1/2 cm) |
| 30x (FIG. 17) | 1-1/2 inches (3-3/4 cm) |
| 40c (FIG. 19) | 9-1/2 inches (24 cm) |
| 40d (FIG. 19) | 3 inches (7-1/2 cm) |
| 40e (FIG. 19) | 11-3/4 inches (29-3/4 cm) |
| 318d (FIG. 19) | 1-3/4 inches (4-1/2 cm) |
| 318wi (FIG. 19) | 9-1/2 inches (24 cm) |
| 318wo (FIG. 19) | 6 inches (15-1/4 cm) |
| 369d (FIG. 17) | 15-3/4 inches (40 cm) |
| 369h (FIG. 17) | 1 inch (2-1/2 cm). |

In actual testing, methodology can include injection of a gas to include a preheated gas, for example, air, into an oleaginous liquid sample, such as known in the art or disclosed in the aforementioned application of Selby et al., where, in general, pristine oil samples are subject to foam testing. However, for alternative foam testing, it may be desirable to introduce one or more contaminant(s) into the sample, especially so that the same has a standardized, predetermined level(s) of contaminant(s). For example, water may be introduced to an oil sample in the form of a liquid before it is heated and air is bubbled through to produce the foam, or, as a preferred alternative, water may be introduced in the gaseous phase. The water vapor may be provided before or during foaming such as by introduction by steam or air which has been moistened by bubbling it through liquid water in an enclosed flask. Other contaminants which may be introduced include fuel, carbon and/or metal particles, silicone-containing anti-foaming agents, and so forth and the like. Accordingly, foam testing can be correlated to the presence of the contaminant(s) in an actual oil sample as found, for example, in internal combustion engines, or in automatic transmission fluids, and so forth, where air contact, combustion by products, wear and tear and other sources of contamination may affect an oil in use.

Accordingly, the oven of the invention, for example, embodied as a foam tester, can heat and cool circulating gas, and hence, contained sample containers, rapidly. A volume for cooling the oven volume is provided apart from the oven volume, and the cooling volume is adapted to contain cooling material, at least during operation of the cooling cycle. Optionally, the cooling volume can be closed off from the oven volume when the device is in heating mode and opened when in cooling mode, but preferably, it is not but has a drainable liquid, for example, water, cooling system installed in the cooling volume. The device may have an air plume; preferably however, it has such a plume eliminated with high circulation blowing and mixing of the bath gas, for example, air, provided. Accessories such as a removable drain tray, and so forth, may be added. The exemplary devices are particularly useful for testing for the foaming characteristics of liquids, and the principles of the cooling volume can be applied to cabinet ovens in general. As an option, gel or cooling other than liquid in radiator cooling, for example, solid state cooling, may be employed. Test methodology can include injection of a gas to include a preheated gas, for example, air, into an oleaginous liquid sample, for example, oil or transmission fluid, especially having standardized, predetermined level(s) of contaminant(s).

CONCLUSION

The present invention is thus provided. Parts and subcombinations may be interchanged from one embodiment to another, and further, may be practiced without regard to other parts, subcombinations or combinations, in the practice of the invention, and numerous adaptations and modifications can be effected within its spirit, the literal claim scope of which is particularly pointed out as follows:

We claim:

1. In a foam tester device including a cabinet with a temperature-regulatable oven volume contained therein, the oven volume being insulated; a heater capable of heating a gas for the oven volume; a feature to circulate heated gas in the oven volume; an access system such that sample container(s), each capable of holding a liquid sample, is(are) insertable into the oven volume so that the same can be heated therein; and a feature to observe any sample(s) in the sample container(s) such that observation can be conducted from outside the cabinet—and wherein a cooling feature is provided to cool down the oven volume in the cabinet—the improvement which comprises a cooling volume apart from the oven volume, the cooling volume containing the cooling feature which has coolant material, wherein the cooling volume is contained within the cabinet, which cooling volume can be closed off from the oven volume when the device is in heating mode and opened to the oven volume when the device is in cooling mode and, when the cooling volume is opened to the oven volume, and wherein the gas for the oven volume can flow through the cooling volume.

2. The device of claim 2, wherein provision is made therein for a sample bubbling gas to provide test foam for the liquid sample(s) in the sample container(s), and the gas is air.

3. The device of claim 2, which has an air plume.

4. The device of claim 3, wherein the cooling feature which has coolant material is provided by a liquid in radiator to air cooling system.

5. The device of claim 3, wherein the cooling feature which has coolant material is provided by gel cooling provided by a gel tube assembly.

6. The device of claim 3, wherein the cooling feature which has coolant material is provided by solid state cooling which includes a ferro-electric unit operating on the Peltier effect.

7. The device of claim 3, wherein the oven volume is defined so that it has imperforate top, front and rear walls, has two side walls with open side wall sections with two opposing openings in upper portions of the side walls and perforate wall sections making up upper near-front and upper rear side wall sections, and imperforate lower side wall sections, behind which are placed insulating tiles and behind which are positioned side channels of a positive pressure plenum, in which are placed heaters for heating the air, has a bottom bounded by an oven volume floor under at least part of which a negative pressure plenum is positioned, which negative pressure plenum has a V-shaped floor defined in part by a groove which can catch and route a liquid spill therein, through a hole in the cabinet, and into a drain tray assembly positioned outside the cabinet; the cooling volume can take in air from outside the cabinet, the cooling volume is adjacent the negative pressure plenum; and a movable door which opens or closes an opening between the cooling volume and the negative pressure plenum is present to provide that the cooling volume can be closed off from the oven volume when the device is in heating mode and opened to the oven volume when the device is in cooling mode; and an insertable carousel is provided to hold the sample container(s).

8. The device of claim 1, wherein the feature to observe any sample(s) in the sample container(s) such that observation can be conducted from outside the cabinet includes a multi-pane, heat-insulating, wide-range-of-view window having an inner and outer window set, in which the inner window is more narrow than the outer window.

9. A foam tester device comprising a cabinet with a temperature-regulatable oven volume contained therein, the oven volume being insulated; a heater capable of heating a gas for the oven volume; a feature to circulate heated gas in the oven volume; an access system such that sample container(s), each capable of holding a liquid sample, is(are) insertable into the oven volume so that the same can be heated therein; a feature to observe any sample(s) in the sample container(s) such that observation can be conducted from outside the cabinet; and a cooling volume contained in the cabinet but apart from the oven volume, the cooling volume containing a cooling feature having coolant material, which cooling volume is not closed off from the oven volume when the device is in heating mode, and which has a drainable liquid cooling system installed in the cooling volume, wherein the cooling volume and the oven volume are in constant communication through at least one blower; and the device is plumeless.

10. The device of claim 9, wherein the feature to circulate air includes at least one high intensity blower, which, when the device is in operation, forces air through a plenum and into the oven volume, and receives the air from the oven volume to recycle the air back into the plenum and oven volume; the cooling is provided by the drainable liquid cooling system, which is installed in the plenum; provision is made for a sample bubbling gas to provide test foam for the liquid sample(s) in the sample container(s), and the gas is air.

11. The device of claim 10, wherein the plenum generally has two communicating components: a vertically directed, upper component and a transversely directed, lower component; the at least one blower is installed in an upper portion of the upper plenum component and receives air from an upper portion of the oven volume; the heater is installed in the upper plenum component below the at least one blower; and the drainable liquid cooling system is installed below the heater.

12. The device of claim 11, wherein the oven volume is defined by an oven volume housing having a rear wall, which is imperforate save a blower intake opening, two imperforate side walls, a top wall, which is imperforate save a carousel access hole, a heat-insulating window, which also can be employed as the feature to observe any sample(s) in the sample container(s), and a floor having a center hole and front and rear air circulation holes in communication with the transversely directed, lower component of the plenum; and an insertable carousel is provided to hold the sample container(s).

13. The device of claim 12, wherein the feature to observe any sample(s) in the sample container(s) such that observation can be conducted from outside the cabinet includes a multi-pane, heat-insulating, wide-range-of-view window having an inner and outer window set, in which the inner window is more narrow than the outer window.

\* \* \* \* \*

UNITED STATES PATENT AND TRADEMARK OFFICE
CERTIFICATE OF CORRECTION

PATENT NO. : 6,009,748
DATED : January 4, 2000
INVENTOR(S) : Hildebrandt et al.

It is certified that error appears in the above-identified patent and that said Letters Patent is hereby corrected as shown below:

Drawings,
Sheet 6 of 14 should be deleted to be replaced with drawing sheet 6 of 14, as shown on the attached page.

Column 16,
Line 49, delete "2," inserting -- 1, -- therefor.

Column 17,
Line 11, after "cabinet," insert -- and --.
Line 13, delete "and" before "a movable door."

Column 18,
Line 11, delete the comma "," of "container(s)," and insert therefor a semicolon -- ; --.

Signed and Sealed this

Sixteenth Day of September, 2003

JAMES E. ROGAN
*Director of the United States Patent and Trademark Office*